US012797638B2

(12) United States Patent
Green et al.

(10) Patent No.: US 12,797,638 B2
(45) Date of Patent: Nov. 17, 2026

(54) THERAPEUTIC DEVICES AND METHODS FOR TREATING CORNEAL ABRASIONS, CORNEAL INFECTIONS, AND PROPHYLAXIS OF CORNEAL INFECTIONS

(71) Applicant: KeraLink International, Inc., Baltimore, MD (US)

(72) Inventors: David Green, Ann Arbor, MI (US); Aaron Chang, Winterville, NC (US); Alexandra Sibole, Fort Collins, CO (US); Ryan Chase Kelley, Denver, CO (US)

(73) Assignee: KERALINK INTERNATIONAL, INC., Baltimore, MD (US)

( * ) Notice: Subject to any disclaimer, the term of this patent is extended or adjusted under 35 U.S.C. 154(b) by 0 days.

(21) Appl. No.: 19/454,958

(22) Filed: Jan. 21, 2026

(65) Prior Publication Data

US 2026/0158291 A1 Jun. 11, 2026

Related U.S. Application Data

(63) Continuation of application No. PCT/US2025/059024, filed on Dec. 10, 2025.

(Continued)

(51) Int. Cl.

*A61N 5/06* (2006.01)
*A61B 3/00* (2006.01)

(Continued)

(52) U.S. Cl.

CPC .......... *A61N 5/0624* (2013.01); *A61B 3/0008* (2013.01); *A61B 3/0025* (2013.01);

(Continued)

(58) Field of Classification Search

None

See application file for complete search history.

(56) References Cited

U.S. PATENT DOCUMENTS 9,474,811 B2 10/2016 Sharma
10,722,180 B2 7/2020 Zhang et al.

(Continued)

FOREIGN PATENT DOCUMENTS

CN 213283747 U 5/2021
WO 2012122210 9/2012

(Continued)

OTHER PUBLICATIONS

International Search Report and Written Opinion for Application No. PCT/US2025/059024, dated Feb. 27, 2026, 15 pages.

*Primary Examiner* — Deborah L Malamud

(74) *Attorney, Agent, or Firm* — William R. Childs; Childs Patent Law PLLC

(57) ABSTRACT

The present disclosure relates to a therapeutic device for treating a corneal abrasion, a corneal infection, or both, where the therapeutic device includes a housing including an eye module, a camera module mounted in the housing and configured to detect light from the eye module, a non-ultraviolet light source configured to direct non-ultraviolet light through the eye module. A benefit of the devices can be to provide targeted, dynamically adaptable treatments to eyes afflicted with corneal abrasions and corneal infections.

19 Claims, 9 Drawing Sheets

Related U.S. Application Data

(60) Provisional application No. 63/730,766, filed on Dec. 11, 2024.

(51) Int. Cl.
*A61B 3/14* (2006.01)
*A61N 5/067* (2006.01)

(52) U.S. Cl.
CPC ................ *A61B 3/14* (2013.01); *A61N 5/067* (2021.08); *A61N 2005/0627* (2013.01); *A61N 2005/063* (2013.01); *A61N 2005/0644* (2013.01); *A61N 2005/0652* (2013.01); *A61N 2005/0659* (2013.01); *A61N 2005/0661* (2013.01); *A61N 2005/0662* (2013.01); *A61N 2005/0666* (2013.01); *A61N 2005/0667* (2013.01)

(56) References Cited

U.S. PATENT DOCUMENTS

| | | | | |
|---|---|---|---|---|
| 12,447,354 | B2 | 10/2025 | Hunter et al. | |
| 2011/0282333 | A1* | 11/2011 | Herekar ................. | A61N 5/062 606/4 |
| 2015/0005750 | A1 | 1/2015 | Kelleher et al. | |
| 2016/0067086 | A1 | 3/2016 | Tedford et al. | |
| 2022/0016439 | A1 | 1/2022 | Shah et al. | |
| 2022/0226522 | A1 | 7/2022 | Kurz et al. | |
| 2022/0313077 | A1 | 10/2022 | Singh et al. | |

FOREIGN PATENT DOCUMENTS

| | | | |
|---|---|---|---|
| WO | 2025059024 | | 3/2025 |
| WO | 2026128623 | A1 | 6/2026 |

* cited by examiner

THERAPEUTIC DEVICES AND METHODS FOR TREATING CORNEAL ABRASIONS, CORNEAL INFECTIONS, AND PROPHYLAXIS OF CORNEAL INFECTIONS

CROSS REFERENCE TO RELATED APPLICATIONS

This application claims priority to Application No. PCT/US25/59024 filed on Dec. 10, 2025, which claims priority to U.S. Provisional Patent Application No. 63/730,766, filed on Dec. 11, 2024, each of which are incorporated by reference in their entirety.

TECHNICAL FIELD

The present disclosure relates generally to the field of medical devices. In particular, the present disclosure provides therapeutic devices for treating corneal abrasions and corneal infections, and methods of treating corneal abrasions and corneal infections using such therapeutic devices. A benefit of the devices can be to provide targeted, dynamically adaptable treatments to eyes afflicted with corneal abrasions and corneal infections.

BACKGROUND

Corneal abrasions and corneal infections are a significant cause of ocular morbidity worldwide. Many corneal abrasions can result in corneal infections, if not treated before infection sets in. These infections can arise from a variety of sources, including bacteria, viruses, fungi, and parasites, which may or may not be introduced during the abrasion event. Current treatment methods for treating corneal abrasions and corneal infections typically involve administering topical, oral, or injectable antimicrobial agents, such as antibiotics, antivirals, or antifungals. However, to treat a corneal abrasion, the site and severity of the corneal abrasion should be identified. Also, should the cornea become infected, then the cause of the infection needs to be identified accurately before corresponding treatments are administered to a human or an animal subject. For example, for infections caused by bacteria, antibiotics are administered. Meanwhile, for infections caused by viruses, antiviral medications are prescribed. Diagnosing the site and severity of a corneal abrasion and identifying the causative infectious microorganism often requires highly trained doctors and laboratory testing, which are expensive, time-consuming and can be inaccurate, yielding false positives or false negatives. Testing also delays the initiation of appropriate treatment, potentially allowing the corneal abrasion to become infected and/or allowing infections to worsen. Furthermore, traditional pharmaceutical treatments can be associated with side effects, requiring prolonged treatment durations, and cannot always achieve complete eradication of the infectious agent. In low-income countries, the expense, often limited availability of treatment, lack of patient compliance to administering treatment and logistics of diagnosing and providing the proper medicine often results in these corneal abrasions going untreated, leading to unnecessary corneal infections, patient suffering and partial or complete blindness. Furthermore, liberal use of broad-spectrum antibiotics, antivirals, and antifungals has been documented to contribute to the problem of antimicrobial resistance.

In view of these limitations, alternative treatment strategies that do not rely on pharmaceutical compositions are needed. Further, treatment strategies are needed that do not require a doctor or are greatly able to reduce the amount of time required by a doctor and/or lab to diagnose and treat corneal abrasions and corneal infections.

UV light, especially far-UVC light, is known to have broad antimicrobial applications. There have been research efforts directed at using UV to treat corneal infections, but certain wavelengths of UV such as UVA and UVB are known to cause cancer and directing UV into the eye can cause tissue damage.

Therefore, there remains a need for a therapeutic method or device that provides solutions to at least the above-mentioned challenges.

SUMMARY

The present disclosure relates to therapeutic devices for treating a corneal abrasion, a corneal infection, or prophylaxis of a corneal infection, or any combination thereof. In some embodiments, the therapeutic devices for treating a corneal abrasion, a corneal infection, or prophylaxis of a corneal infection, or any combination thereof, include: a housing including an eye module; a camera module mounted in the housing and configured to detect light from the eye module; a non-ultraviolet light source configured to direct non-ultraviolet light through the eye module; and an ultraviolet light source configured to direct ultraviolet light through the eye module at an ultraviolet wavelength, an ultraviolet intensity, and an ultraviolet angle of incidence, wherein the ultraviolet light source is configured to change the ultraviolet wavelength within an ultraviolet range of from about 200 nm to about 300 nm, to change the ultraviolet intensity within an ultraviolet intensity range of from about 2.0 $mJ/cm^2$ to about 1,500 $mJ/cm^2$, or to change the ultraviolet angle of incidence within an ultraviolet angle range of from 0° to 90°, or any combination thereof.

In some embodiments of the therapeutic device, the eye module is located on an exterior of the housing and includes a light source opening surrounded by an eye adapter, wherein the eye adapter has a ring shape with a raised lip surrounding an eye adapter recess, wherein the eye adapter recess surrounds the light source opening; and wherein the raised lip has a lip diameter or a lip longest distance across the eye adapter of from about 40.0 mm to about 60.0 mm; or wherein the eye adapter recess has an eye adapter depth of about 1.0 cm to about 5.0 cm from the raised lip to the light source opening; or wherein the therapeutic device has a device weight of about 227.0 g to about 1,360.0 g. In some embodiments, the therapeutic device further includes a UV mirror, wherein the UV mirror includes a dichroic mirror or a metal-containing mirror, wherein the ultraviolet light source includes an array of ultraviolet light emitting diodes, an excimer lamp, a laser, or a combination thereof; wherein the UV mirror is configured to direct non-ultraviolet light from the non-ultraviolet light source through the eye module; or wherein the UV mirror is configured to direct the ultraviolet light from the ultraviolet light source through the eye module; or wherein the UV mirror is configured to simultaneously direct non-ultraviolet light from the non-ultraviolet light source and the ultraviolet light from the ultraviolet light source through the eye module; or wherein the UV mirror is located between the eye module and the camera module; or wherein the UV mirror is located between the eye module and the ultraviolet light source; or wherein the housing contains an actuator adjustable focal lens, a frequency doubler, a triple filter, one or more rotatable filters, a mechanically rotatable filter, or an aperture, or a combination thereof, located between the eye module and the ultraviolet light source, and one or more of the actuator adjustable focal lens, the frequency doubler, the triple filter, one or more rotatable filters, the mechanically rotatable filter, the aperture, or the combination thereof, are configured to change the ultraviolet wavelength, the ultraviolet intensity, or the ultraviolet angle of incidence, or any combination thereof, or wherein the housing contains an actuator a frequency doubler, a mechanically rotatable filter, or both, located between the eye module and the non-ultraviolet light source, and configured to convert the non-ultraviolet light into the ultraviolet light; or any combination thereof. In some embodiments of the therapeutic device, the eye module includes an array of optical fibers, wherein the array of optical fibers is operatively connected to the ultraviolet light source, wherein the ultraviolet light source includes an array of ultraviolet light emitting diodes, an excimer lamp, a laser, or a combination thereof; wherein emitting portions of the array of optical fibers are mounted around an eye adapter interior surface of the eye module; wherein an eye module actuator is operatively connected to the eye adapter, the emitting portions, or any combination thereof; and wherein the eye module actuator is configured to change the ultraviolet angle of incidence from the emitting portions by moving the emitting portions along the eye module interior surface; or wherein the eye module actuator is configured to change the ultraviolet angle of incidence from the emitting portions by moving the eye adapter; or wherein the eye module contains one or more movable reflectors capable of changing the angle of incidence relative to the emitting portions; or any combination thereof. In some embodiments of the therapeutic device, the ultraviolet light source includes an array of ultraviolet light emitting diodes mounted around an eye adapter interior surface of the eye module, wherein an ultraviolet light emitting diode of the array of ultraviolet light emitting diodes is mounted on an actuator track, and wherein the ultraviolet light emitting diode is configured to change the ultraviolet angle of incidence by moving the ultraviolet light emitting diode along the actuator track; or wherein two or more ultraviolet light emitting diodes of the array of ultraviolet light emitting diodes are mounted on an actuator track, and the two or more ultraviolet light emitting diodes are configured to change the ultraviolet wavelength, the ultraviolet intensity, or the ultraviolet angle of incidence, or any combination thereof, by turning on or off. In some embodiments of the therapeutic device, the ultraviolet light source includes an array of ultraviolet light emitting diodes mounted around an eye adapter interior surface of the eye module, wherein two or more ultraviolet light emitting diodes of the array of ultraviolet light emitting diodes are configured to change the ultraviolet wavelength, the ultraviolet intensity, or the ultraviolet angle of incidence, or any combination thereof, by turning on or off. In some embodiments of the therapeutic device, the housing contains a camera module opening surrounding a lens of the camera module, and wherein the non-ultraviolet light source includes a visible light emitting diode, an infrared light emitting diode, an array of visible light emitting diodes, an array infrared light emitting diodes, or a combined array of visible light emitting diodes and infrared light emitting diodes, or any combination thereof, or wherein the non-ultraviolet light source includes a visible light emitting diode capable of emitting light at a visible wavelength of from about 400 nm to about 700 nm; or wherein the non-ultraviolet light source includes an infrared light emitting diode capable of emitting an infrared light at a wavelength of from about 780 nm to about 1,000 nm; or wherein the non-ultraviolet light source is located adjacent to a lens of the camera module; or wherein the non-ultraviolet light source includes an array of visible light emitting diodes adjacent to or round a lens of the camera module; wherein the non-ultraviolet light source includes an array of infrared light emitting diodes adjacent to or round a lens of the camera module; or any combination thereof. In some embodiments of the therapeutic device, the housing contains a processor, wherein the processor is operatively connected to the ultraviolet light source, the non-ultraviolet light source, the camera module, or the eye module, or any combination thereof, and wherein the processor is configured to change the ultraviolet wavelength, the ultraviolet intensity, or the ultraviolet angle of incidence, or any combination thereof, during an adjustment duration of from about 0.1 second to about 2.0 minutes by executing a computer readable code; or wherein the housing contains a processor, wherein the processor is operatively connected to a control panel located on the device exterior, or wherein the processor is operatively connected to at least one communication link, or any combination thereof, wherein the communication link includes a short-range wireless connection, a universal serial bus (USB) connection, or a data port; or wherein the camera module includes a charged coupled device or a complementary metal oxide semiconductor (CMOS) image sensor; or a camera lens configured to focus light at a distance of from about 1.0 cm to about 25.0 cm from a surface of the camera lens; or the camera module includes a light transparent protective cover between a surface of the camera lens and the eye module; or wherein the housing contains the ultraviolet light source and the non-ultraviolet light source and one or both of the ultraviolet light source and the non-ultraviolet light source are configured to move along a track or to change ultraviolet intensity or both; or any combination thereof. In some embodiments of the therapeutic device, the ultraviolet light source includes an array of ultraviolet light emitting diodes mounted around an eye adapter interior surface of the eye module, or mounted within the housing and directed toward the light source opening, or both; and wherein two or more ultraviolet light emitting diodes of the array of ultraviolet light emitting diodes are configured to change the ultraviolet wavelength, the ultraviolet intensity, or the ultraviolet angle of incidence, or any combination thereof, by turning on or off; or wherein the ultraviolet light source includes an array of ultraviolet light emitting diodes and a non-ultraviolet light source mounted around an eye adapter interior surface of the eye module, or mounted within the housing and directed toward the light source opening, or both; and wherein two or more ultraviolet light emitting diodes of the array of ultraviolet light emitting diodes are configured to change the ultraviolet wavelength, the ultraviolet intensity, or the ultraviolet angle of incidence, or any combination thereof, by turning on or off.

The present disclosure relates to methods of detecting or treating a corneal abrasion, a corneal infection, or prophylaxis of a corneal infection, or any combination thereof. In some embodiments, the method includes providing a therapeutic device, wherein the therapeutic device includes, a housing including an eye module; a camera module mounted in the housing and configured to detect light from the eye module; a non-ultraviolet light source configured to direct non-ultraviolet light through the eye module; and an ultraviolet light source configured to direct ultraviolet light through the eye module at an ultraviolet wavelength, an ultraviolet intensity, and an ultraviolet angle of incidence, wherein the ultraviolet light source is configured to change the ultraviolet wavelength within an ultraviolet range of from about 200 nm to about 300 nm, to change the ultraviolet intensity within an ultraviolet intensity range of from about 2.0 mJ/cm$^2$ to about 1,500 mJ/cm$^2$, or to change the ultraviolet angle of incidence within an ultraviolet angle range of from 0° to 90°, or any combination thereof; and directing the ultraviolet light into the eye of the subject at the ultraviolet wavelength, the ultraviolet intensity, or the ultraviolet angle of incidence, or any combination thereof, for a therapeutic duration.

In some embodiments of the method, the therapeutic duration is from about 1.0 second to about 5.0 minutes; or further comprising, changing the ultraviolet wavelength, the ultraviolet intensity, or the ultraviolet angle of incidence, or any combination thereof, during an adjustment duration of from about 0.1 second to about 2.0 minutes before, during, or after the therapeutic duration; or wherein the subject is a human being or a mammal. In some embodiments, the method further includes before, during, or after directing the ultraviolet light into the eye of the subject, reducing inflammation or microbial burden; or treating a wound by directing the non-ultraviolet light, including infrared light, into the eye of the subject; or before or during directing the ultraviolet light into the eye of the subject, contacting the eye of the subject with hypochlorous acid; locating an infection area of the eye of the subject and directing the ultraviolet light onto the infection area; or locating and mapping an infection area of the eye of the subject by directing the non-ultraviolet light into the eye of the subject and changing the ultraviolet wavelength, the ultraviolet intensity, or the ultraviolet angle of incidence, or any combination thereof; or wherein the housing contains a processor, wherein the processor is operatively connected to the ultraviolet light source, the non-ultraviolet light source, the camera module, or the eye module, or any combination thereof, and changing the ultraviolet wavelength, the ultraviolet intensity, or the ultraviolet angle of incidence, or any combination thereof, during an adjustment duration of from about 0.10 second to about 2.0 minutes by executing a machine-readable code; or wherein the housing contains a processor, wherein the processor is operatively connected to the ultraviolet light source, the non-ultraviolet light source, the camera module, or the eye module, or any combination thereof, and changing the ultraviolet wavelength, the ultraviolet intensity, or the ultraviolet angle of incidence, or any combination thereof, during an adjustment duration of from about 0.10 second to about 2.0 minutes by transmitting a signal from the processor to an actuator, wherein the actuator is operatively connected to the ultraviolet light source, the non-ultraviolet light source, the camera module, or the eye module, or any combination thereof. In some embodiments of the method, the housing contains a processor, diagnosing the corneal infection by; directing the non-ultraviolet light into the eye of the subject, detecting a reflected light from the eye of the subject in the camera module, and gathering reflected light data by measuring a reflected wavelength, a reflected intensity, and a reflected light position within an area of the eye of the subject, comparing the reflected light data to a database of corneal infections; and forming a diagnosis by comparing the reflected light data to a type of corneal infection; or forming an infection area data map of the eye by comparing the reflected light data to normal eye data, a database of corneal infections, or both; or any combination thereof. In some embodiments, the method further includes after forming the diagnosis, changing the ultraviolet wavelength, the ultraviolet intensity, or the ultraviolet angle of incidence, or any combination thereof, based on the reflected light data, the type of corneal infection, or both; or after forming the infection area map, directing from about 50% to 100% of the ultraviolet light onto a mapped infection area of the eye of the subject, wherein the mapped infection area of the eye corresponds to or matches the infection area data map; or any combination thereof. In some embodiments, the method further includes before, during, or after directing the ultraviolet light into the eye of the subject, directing the non-ultraviolet light into the eye of the subject; or locating an abraded area of the eye of the subject and directing the ultraviolet light, infrared light, or both, onto the abraded area; or locating an abraded area of the eye of the subject by directing the non-ultraviolet light into the eye of the subject and changing the ultraviolet wavelength, the ultraviolet intensity, or the ultraviolet angle of incidence, the infrared wavelength, the infrared intensity, or the infrared angle of incidence, or any combination thereof, or wherein the housing contains a processor, wherein the processor is operatively connected to the ultraviolet light source, the non-ultraviolet light source, the camera module, or the eye module, or any combination thereof, and changing the ultraviolet wavelength, the ultraviolet intensity, or the ultraviolet angle of incidence, or any combination thereof, during an adjustment duration of from about 0.10 second to about 2.0 minutes by executing a machine-readable code; or wherein the housing contains a processor, wherein the processor is operatively connected to the ultraviolet light source, the non-ultraviolet light source, the camera module, or the eye module, or any combination thereof, and changing the ultraviolet wavelength, the ultraviolet intensity, or the ultraviolet angle of incidence, or any combination thereof, during an adjustment duration of from about 0.10 second to about 2.0 minutes by transmitting a signal from the processor to an actuator, wherein the actuator is operatively connected to the ultraviolet light source, the non-ultraviolet light source, the camera module, or the eye module, or any combination thereof.

BRIEF DESCRIPTION OF THE DRAWINGS

The foregoing summary, as well as the following detailed description of the embodiments, will be better understood when read in conjunction with the attached drawings. For the purpose of illustration and evidence, there are shown in the drawings some embodiments, which can be preferable. It should be understood that the embodiments depicted are not limited to the precise details shown and are not drawn to scale.

DETAILED DESCRIPTION

Figure 1B:
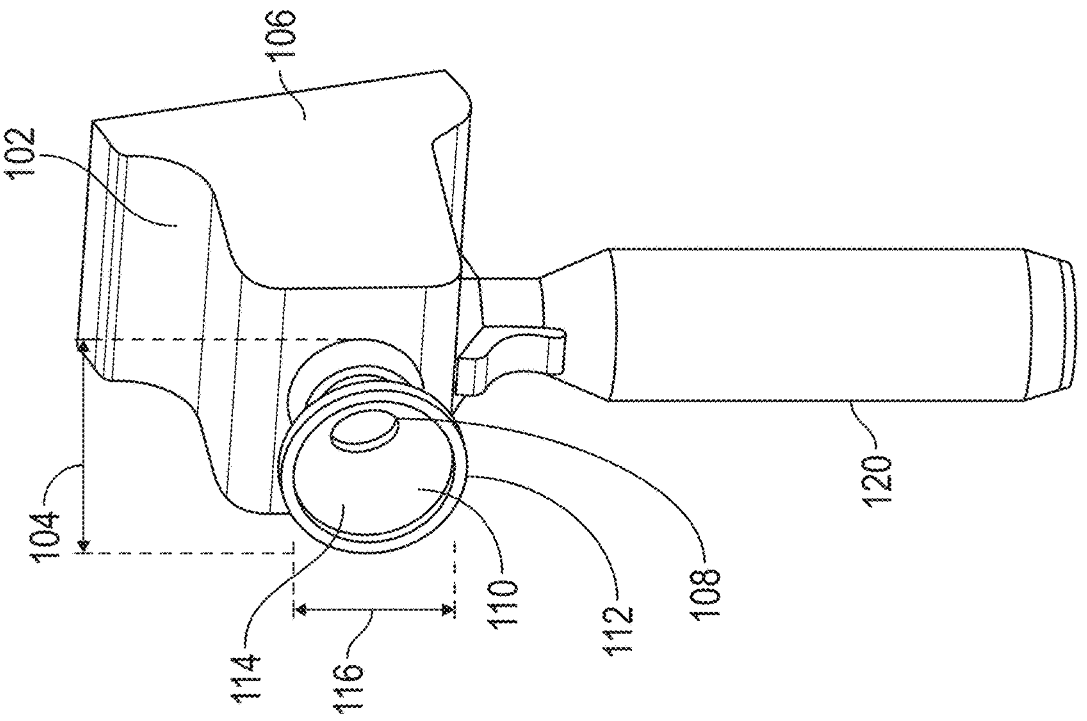
FIGS. 1A and 1B are schematic depictions of embodiments of a therapeutic device for treating corneal abrasions and corneal infections.

Unless otherwise noted, all measurements are in standard metric units.

Unless otherwise noted, all instances of the words "a," "an," or "the" can refer to one or more than one of the words that they modify.

In this application, the use of "or" means "and/or", unless specifically stated otherwise.

Unless otherwise noted, the use of the term "including", as well as other forms, such as "includes" and "included", is not limiting.

Unless otherwise noted, the use of the term "comprising", as well as other forms, such as "comprise" or "comprises", is not limiting.

Unless otherwise noted, when the term "diameter" refers to a circular shape or opening, then the diameter refers to a longest distance across the circular shape or face. When the term "diameter" refers to a shape or opening having a non-circular shape, then the term "diameter" refers to a longest distance across the non-circular shape or opening. Examples of non-circular shapes include an oval or ellipse, a square, a hexagon, an octagon, or any polygon.

Unless otherwise noted, the term "about" refers to ±10% of the non-percentage number that is described, rounded to the nearest number to the accuracy shown. For example, about 105.3 mm, would include 94.8 to 115.8 mm. Unless otherwise noted, the term "about" refers to ±5% of a percentage number. For example, about 20% can include from 15 to 25%. When the term "about" is discussed in terms of a range, then the term refers to the appropriate amount less than the lower limit and more than the upper limit. For example, from about 100 g to about 200 g can include from 90 to 220 g.

Unless otherwise noted, if a number is easily variable in a laboratory setting (length, weight, pressure, voltage etc.), then a range of numbers includes all numbers in that range. For example, the range of 0.01 V to about 12 V includes 0.05, 0.1, 0.5, 1, 2, 3.5, 5, 6.75, 8.5, 10 and any sub-range therein.

Unless otherwise noted, the phrase "at least one of" means one or more than one of an object. For example, "at least one of a UV lamp and a UV diode" means a single UV lamp, two UV lamps, a single UV diode, two UV diodes, three UV diodes, or any combination or sub-combination thereof.

Unless otherwise noted, the terms "provide", "provided" or "providing" refer to the supply, production, purchase, manufacture, assembly, formation, selection, configuration, conversion, introduction, addition, or incorporation of any element, amount, component, reagent, quantity, measurement, or analysis of any method or system of any embodiment herein.

Unless otherwise noted, the term "real time" means from instantly to 2 hours.

The term "for example" or "e.g.," as used herein, is used merely by way of example, without limitation intended, and should not be construed as referring to only those items explicitly enumerated in the specification.

Unless otherwise noted, the term "operatively connected" refers to a direct or indirect connection that allows for the two or more connected objects to operate together to perform a function, wherein the function depends on the context of the objects. For example, an array of optical fibers is "operatively connected" to the ultraviolet light source, where the array connects by an optical pathway such that optical fibers are capable of transmitting light from the ultraviolet light source. An eye module actuator is "operatively connected" to the eye adapter, where the eye module actuator can move the eye adapter directly or cause movement of the eye adapter by moving an intermediate component. A processor is "operatively connected" to a control panel, where the processor is connected by a signal pathway (electrical, optical, transmitter/receiver) such that the processor can send a signal to or receive a signal from the control panel.

The term "configured" refers to a position, arrangement, or orientation of the subject relative to an object another so that the configured subject can perform a function, and wherein the function depends on the context of the subject and object. For example, the phrase "ultraviolet light source configured to direct ultraviolet light through the eye module" means that the ultraviolet light source (subject) is positioned, arranged, or orientated in such a way as to direct light from the ultraviolet light source directly through the eye module (object) or indirectly via an intermediate light manipulating object such as a lens, mirror, or the like. This definition applies when the term "configured" is used in the context of detecting light, directing light, focusing light, or the like. For example, the phrase "ultraviolet light source is configured to change" one or more of the spectral parameters, then the ultraviolet light source is capable of being turned on and off, moved, or even brightened or dimmed by action of operatively connected actuator (such as a motor), an electrical lead operatively connected to a processor, or both.

One way of configuring a light source to change one or more spectral parameters would be to provide an array of light sources (a portion of which are capable of emitting light at different wavelengths), then turn on or off, or dim or brighten one or members of the array to change the intensity or angle of the light emitted relative to the eye module or eye of a subject. Another way of configuring a light source to change a spectral parameter would be to move the light source, such as providing an actuator, such as a track and motor, to physically move an LED or fiber optic or lens to direct light toward the eye module or eye of a subject at different angle.

The terms "UV" and "ultraviolet" are used interchangeably throughout and refers to light having a wavelength of from about 200 nm to 400 nm.

The terms "ultraviolet wavelength" and "ultraviolet wavelength subset" are, or can be, used interchangeably throughout and refer to a subset or narrower range of ultraviolet light wavelengths selected from a range of possible ultraviolet light ultraviolet wavelengths.

The terms "ultraviolet intensity" and "ultraviolet intensity subset" are, or can be, used interchangeably throughout and refer to a subset or narrower range of ultraviolet light intensities that are conducive to the treatment of ocular infections, selected from a range of possible ultraviolet light intensities.

The terms "ultraviolet angle of incidence" and "ultraviolet angle of incidence subset" are, or can be, used interchangeably throughout and refer to a subset or narrower range of angles of incidences in which the ultraviolet light can be emitted, selected from a range of angle of incidences.

The term "spectral parameters" refers to any one or a combination of wavelength, intensity, angle, or any combination thereof, associated with ultraviolet light or non-ultraviolet light.

Corneal abrasions and corneal infections represent a significant challenge in eye care, requiring precise and effective treatment methods. Many corneal abrasions go untreated and develop into corneal infections. Traditional methods of treating corneal infections, such as the administration of antimicrobial agents (antibiotics, antivirals, or antifungals), depend heavily on the accurate identification of the infectious microorganisms, which can delay treatment initiation, potentially allowing the infection to progress. Furthermore, these treatments can be associated with side effects, require a long duration for effectiveness, and cannot always completely eradicate the infectious agents. By destroying pathogens before infection occurs, patients can avoid the pain, irritation, and vision impairment caused by corneal ulcers, removing or reducing the need for traditional anti-microbial treatment.

Ultraviolet (UV) light treatment offers a non-pharmaceutical alternative, capable of neutralizing various microorganisms by damaging their genetic structures. In particular, short-wavelength UV light (UVC), can neutralize a broad spectrum of microorganisms, because exposure to UVC light damages genetic structures (such as deoxyribonucleic acid) of the infectious microorganisms, thereby disrupting replication, weakening, and/or killing them. Unfortunately, certain wavelengths of UV that can damage the genetic structures of microbes can also damage the genetic structures of undamaged and uninfected eye tissues, leading to cell death, tissue damage, and even cancer.

Conventional devices and methods for treating abrasions and/or treating infections in the eye rely on shining UV at damaging wavelengths across the entire eye, or a portion of the eye, using a device that provides UV at a constant wavelength, angle, and/or intensity, regardless of the position of the abrasion, infection, or the type of the infection. While effective for neutralizing microorganisms, this poorly controlled exposure to UV light can cause damage to the other tissues of the eye. For example, if the UV is directed at an angle such that it enters the eye through the pupil, the device runs the risk of burning parts or portions of the retina, which could lead to vision loss. Further, subjects can involuntarily move their eyes, which can cause unaffected portions of the eyes to be exposed to UV light, which is undesirable.

Conventional UV medical devices often do not possess the ability to determine, or assist with determining, where the site of a corneal abrasion occurred. Further, conventional UV medical devices often do not possess the ability to determine or assist with determining which spectral parameters should be adjusted for optimal treatment outcomes for the specific infection of individual subjects. Typically, a doctor, such as a surgeon, has to examine the eye area either manually or using other specialized tools to diagnose the location of an abrasion and/or, infection, and, if the site is already infected, determine if the infection is responsive to the UV light treatment. Based on this diagnosis and observation, the doctor then determines whether any of the spectral parameters are to be increased or decreased based on the infection's response to treatment. Surgeons often rely on intuition rather than mathematical calculations for such assessments, which makes the treatments prone to human error. Also, surgeons typically require aid from a technician or a manufacturer of the device to manually adjust the spectral parameters, which can further increase chances of human error, increase treatment duration and delays, and lower treatment efficacy.

Conventional UV medical devices tend to require specialized equipment and expertise to use. For example, conventional UV medical devices, such as those used for crosslinking or LASIK (Laser-Assisted In Situ Keratomileusis), are typically implemented as fixed or stationary devices that are mounted or installed in a particular location (such as a hospital). Thus, many of these devices are not portable. For example, a UV-emitting diode or UV source can be attached to devices, like traditional slit-lamp devices, which are fixed to a chair or a permanent fixture. While slit-lamp devices offer some flexibility in positioning, their design inherently restricts them from being readily portable or handheld. Also, conventional UV devices provide little or no assistance to the operator, requiring doctors or medical workers to undergo extensive training to be able to safely and effectively use such conventional UV devices. In low-income countries, the inability to provide access to stationary devices and highly specialized medical workers can prevent or reduce the availability of those treatments to people who are poor and/or live in remote areas. Thus, a handheld or portable device would be desirable for improved accessibility, enabling treatment in a wider range of settings, including at a subject's bedside or in areas with limited medical infrastructure. Further, it would be highly desirable if the device were capable of being safely and accurately used by operators with little or no training. Moreover, conventional UV medical devices lack the ability to adjust or change different spectral parameters or attributes of UV light, such as intensity, wavelength, or angle of incidence, among other parameters, in real-time. While some conventional UV medical devices can allow for the adjustment of spectral parameters, such adjustments cannot be made in real-time or during treatment.

It has been discovered that it is possible to provide a therapeutic device that can control and dynamically change the wavelength, intensity, and/or angle of incidence of UV and IR light in real-time. Further, it has been discovered that the therapeutic device can be developed into a "smart device," which can perform or assist with providing both diagnostic and therapeutic functions. The ability to identify or map abrasion sites and infection areas, differentiate between different types of infectious pathogens (e.g. bacteria, viruses, and fungi), observe efficacy, and dynamically change the wavelength, intensity, and/or angle of incidence of both the ultraviolet and infrared light in real-time is a game changer because it can unlock levels of efficacy in treating corneal abrasions and corneal infections that were previously impossible. Better yet, it has been discovered that such therapeutic devices can be portable, making them vastly more accessible to people in low-income countries.

In more detail, therapeutic devices disclosed herein addresses these problems by providing a portable device capable of providing real-time adaptable methods for treating corneal abrasions, corneal infections, or both using UV and IR light. In some embodiments, the therapeutic device includes an eye module with dichroic mirrors, arrays of UV and IR light sources, and the like, that allow spectral parameters or attributes of UV and IR light, such as subsets of wavelength, intensity, and angle of incidence, to be changed or adjusted based on treatment requirements. Adjusting the spectral parameters can enable medical professionals to tailor the specific treatment methodology to the location of the abrasion, and the type, stage, and location of the infection, enhancing the effectiveness of the therapy while minimizing potential side effects. In embodiments of the therapeutic device such adaptability is further supported by the incorporation of a camera module within the device, which aids in diagnosing the infection by analyzing the eye's response to the initial exposure of IR or UV light. The therapeutic device's diagnostic capability may allow for real-time feedback on the treatment's application and efficacy, enabling subsequent adjustments to the UV light's spectral parameters for optimally targeted therapy. Also, built-in diagnostic can reduce the risk of human error and unnecessary exposure to UV light, given that the assessment of treatment efficacy and adjustment of the spectral parameters is otherwise done manually based on the intuition of medical professionals. In some embodiments of the therapeutic device, the eye module can ensure that the treatment is localized only to abrasion areas and infected areas through the use of non-UV light, including infrared light, to align and/or position the device such that the UV light is only directed toward the scratched or infected portions, reducing potential damage to surrounding tissues. In other embodiments of the therapeutic device, the irradiance of the abrasion and infected areas by IR light can add an additional anti-inflammatory and therapeutic wound healing effect. By harnessing the power of computer readable codes, including artificial intelligence, in some embodiments, the therapeutic devices can be safely and effectively used by operators with little or no training. Additionally, the device's design makes it portable and versatile for use in various settings, outside of traditional clinical environments. This combination of the portability of these devices plus computer-assisted diagnosis and directed treatment can greatly improve their accessibility to people in remote areas and low-income countries.

Therapeutic Devices

Embodiments of a therapeutic device are disclosed herein. In some embodiments, the therapeutic device includes a housing including an eye module; a camera module mounted in the housing and configured to detect light from the eye module; a non-ultraviolet light source configured to direct non-ultraviolet light through the eye module; and an ultraviolet light source configured to direct ultraviolet light through the eye module at an ultraviolet wavelength, an ultraviolet intensity, and an ultraviolet angle of incidence, wherein the ultraviolet light source is or can be configured to change the ultraviolet wavelength within an ultraviolet range of from about 200 nm to about 300 nm, to change the ultraviolet intensity within an ultraviolet intensity range of from about 2.0 mJ/cm$^2$ to about 1,500 mJ/cm$^2$, or to change the ultraviolet angle of incidence within an ultraviolet angle range of from 0° to 90°, or any combination thereof.

Figure 1A:
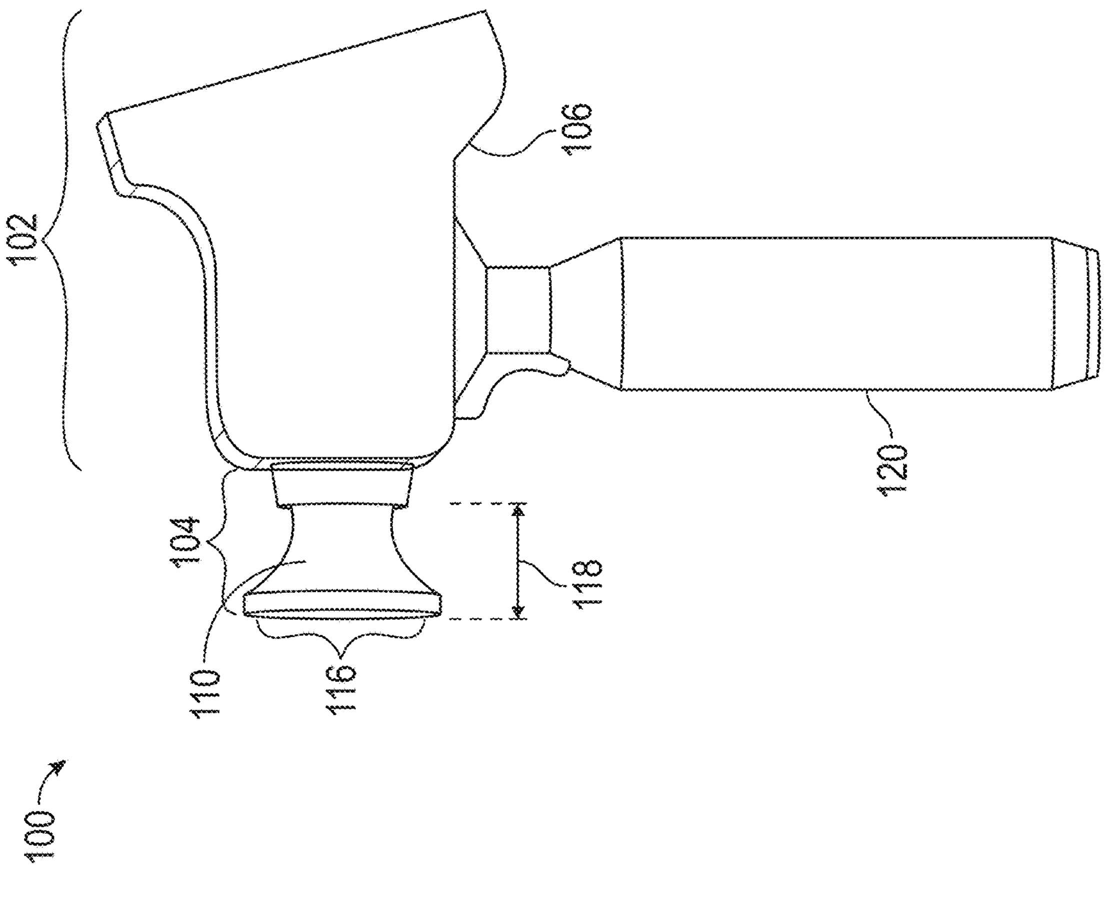

Referring to FIGS. 1A and 1B, in some embodiments, a therapeutic device 100 for treating corneal abrasions and corneal infections, includes a housing 102, which further includes an eye module 104. In some embodiments, the housing includes an exterior 106 of the housing. In some embodiments, the eye module is or can be located on the exterior of the housing. In some embodiments, the eye module includes a light source opening 108 surrounded by an eye adapter 110. In the embodiment shown, the eye adapter has a ring shape with a raised lip 112 surrounding an eye adapter recess 114, wherein the eye adapter recess surrounds the light source opening. In the embodiment shown, the raised lip has a lip diameter 116 (raised lip internal diameter), or a lip longest distance across the eye adapter, of from about 40.0 mm to about 60.0 mm. In some embodiments, the eye adapter recess has an eye adapter depth 118 of about 1.0 cm to about 5.0 cm from the raised lip to the light source opening. In some embodiments, the eye adapter depth is or can be between 2.0 cm to about 4.5 cm. In other embodiments, the eye adapter can have any one or a combination of a cylindrical shape, a frustoconical shape, or a taper shape. In some embodiments, the eye adapter allows ultraviolet light and/or non-ultraviolet light to pass therethrough. In some embodiments, the ultraviolet light and/or the non-ultraviolet light can exit the eye adapter through the light source opening. In some embodiments, the eye adapter can be adapted to provide an interface between an eye of a human or an animal subject and the therapeutic device 100. Further, non-ultraviolet light can aid in aligning the eye of the subject with the therapeutic device 100 in addition to identifying and illuminating the infection to enables machine-readable identification of infectious areas. In some embodiments, the subject can be tasked to focus on the non-ultraviolet light, while the ultraviolet light is or can be irradiated on a different portion of the eye, thereby preventing the ultraviolet light from entering into the eye through the pupil and damaging other tissues therein. In other embodiments, the non-ultraviolet light can be pointed at the eye of the subject by medical professionals to change the angle of the therapeutic device 100 based on where the non-ultraviolet light falls on the eye. In further embodiments, the non-ultraviolet light can encompass IR wavelengths to provide anti-inflammatory and wound healing therapeutic effects to complement the disinfection effects of UV wavelengths.

In some embodiments, the housing further includes a handle 120. In some embodiments, the handle extends out from the exterior in a direction perpendicular or about perpendicular to that of the eye adapter. In some embodiments, the handle enables an operator (such as a surgeon or nurse) to hold the therapeutic device 100 by hand to administer the treatment, thereby allowing the therapeutic device to be conveniently portable. In some embodiments, the therapeutic device 100 has a device weight of about 227.0 g to about 1,360.0 g.

Figure 2:
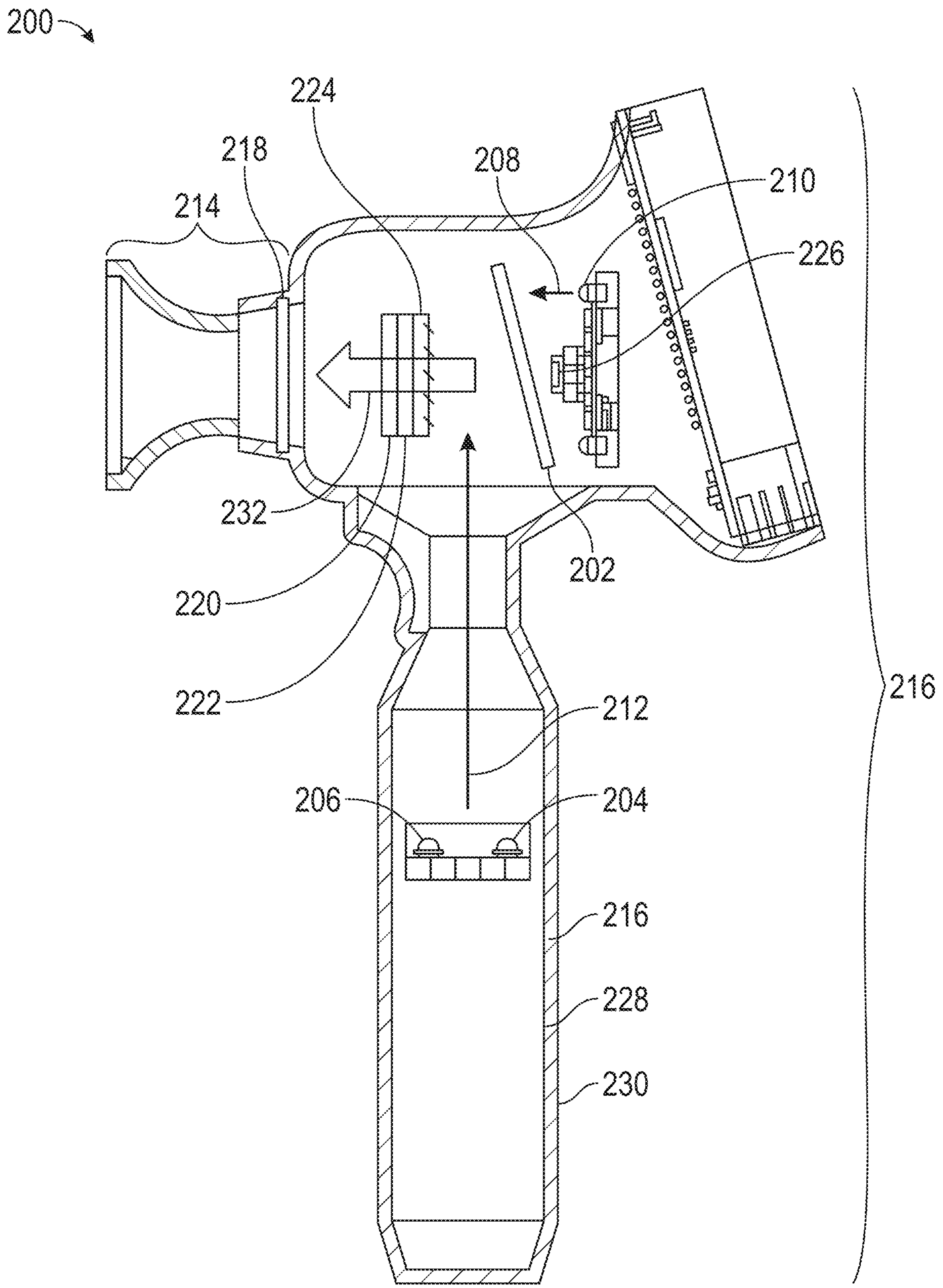
FIG. 2 is a schematic cross-sectional depiction of an embodiment of the therapeutic device.

Referring to FIG. 2, in some embodiments, a therapeutic device 200 includes a non-ultraviolet light source 210 configured to direct non-ultraviolet light 208 through an eye module 214, and an ultraviolet light source 204, 206 (first ultraviolet light source 204 and second ultraviolet light source 206) configured to direct ultraviolet light 212 through the eye module at an ultraviolet wavelength, an ultraviolet intensity, and an ultraviolet angle of incidence. In some embodiments, the non-ultraviolet light can include infra-red light, visible light, or the like, but not limited thereto. In some embodiments, the ultraviolet light source is or can be configured to change the ultraviolet wavelength or ultraviolet wavelength subset within an ultraviolet wavelength range of from about 200 nm to about 300 nm, to change the ultraviolet intensity or ultraviolet intensity subset within an ultraviolet intensity range of from about 2.0 mJ/cm$^2$ to about 1,500 mJ/cm$^2$, or to change the ultraviolet angle of incidence or ultraviolet angle of incidence subset within an ultraviolet angle range of from 0° to 90°, or any combination thereof. In some embodiments, the ultraviolet light source includes an array of ultraviolet light emitting diodes, an excimer lamp (not shown), a laser (not shown), or any combination thereof.

In some embodiments, the therapeutic device 200 further includes a dichroic mirror 202. In some embodiments, the dichroic mirror includes a reflective surface configured to selectively reflect at least one of: the ultraviolet light and/or the non-ultraviolet light. In some embodiments, the dichroic mirror is configured to direct non-ultraviolet light from the non-ultraviolet light source through the eye module. In some embodiments, the dichroic mirror is configured to direct the ultraviolet light from the ultraviolet light source through the eye module. In some embodiments, the dichroic mirror is configured to simultaneously direct the combined light 232 of non-ultraviolet light from the non-ultraviolet light source and the ultraviolet light from the ultraviolet light source, through the eye module. In some embodiments, the ultraviolet light and/or the non-ultraviolet light can be directed towards an eye of a human or an animal subject.

In some embodiments, the dichroic mirror is located between the eye module and the ultraviolet light source. In some embodiments, the therapeutic device 200 further includes a camera module 226 mounted in a housing 216 of the therapeutic device 200, and configured to detect light from the eye module. In some embodiments, the dichroic mirror is located between the eye module and the camera module. In some embodiments, the camera module can be configured to receive or detect the ultraviolet light and/or the non-ultraviolet light reflected from the subject. In some embodiments, the camera module can be configured to collect, store, process, or determine spectral parameters of the ultraviolet light and/or the non-ultraviolet light to be adjected based on those received by the camera module.

In some embodiments, the housing 216 includes a housing interior surface 228 and a housing exterior surface 230. In some embodiments, the housing 216 contains an actuator adjustable focal lens 218, a frequency doubler 220, a mechanically rotatable filter 222, or an aperture 224, or a combination thereof, located between the eye module and the ultraviolet light source. In some embodiments, one or more of the actuator adjustable focal lens, the frequency doubler, the mechanically rotatable filter, the aperture, or the combination thereof, are configured to change the ultraviolet wavelength, the ultraviolet intensity, or the ultraviolet angle of incidence (i.e., the spectral parameters), or any combination thereof. In other embodiments, the housing 216 contains the frequency doubler, the mechanically rotatable filter, or both, located between the eye module and the non-ultraviolet light source, and configured to convert the non-ultraviolet light into the ultraviolet light. In some embodiments, the actuator adjustable focal lens, the frequency doubler, the mechanically rotatable filter, or the aperture can be controlled in real-time, either manually or by an actuator. In some embodiments, the actuator can be a controller that operates similarly to an autofocus lens of cameras.

Figure 3B:
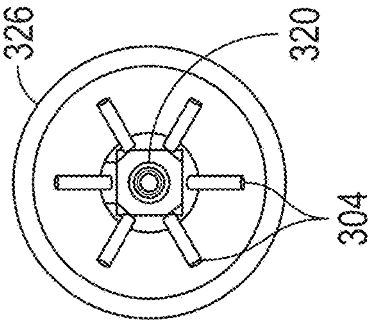
FIG. 3B is a schematic depiction of a straight-on view of an eye adapter of the therapeutic device shown in FIG. 3A.
Figure 3C:
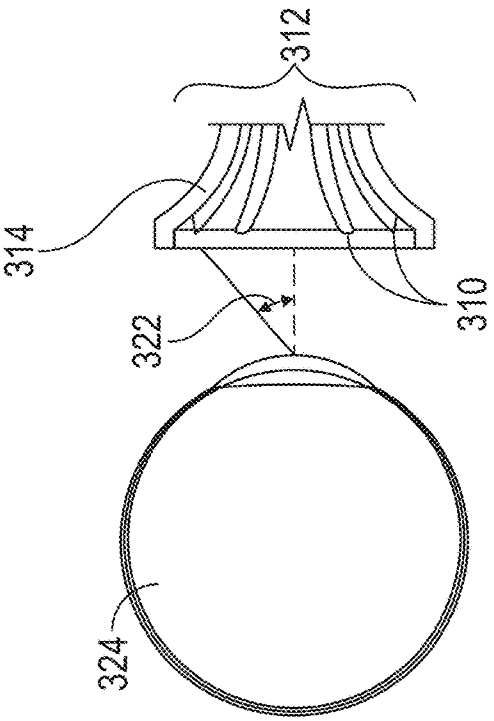
FIG. 3C is a schematic depiction of an angle of incidence of ultraviolet (UV) light emitted from the therapeutic device shown in FIG. 3A.
Figure 3A:
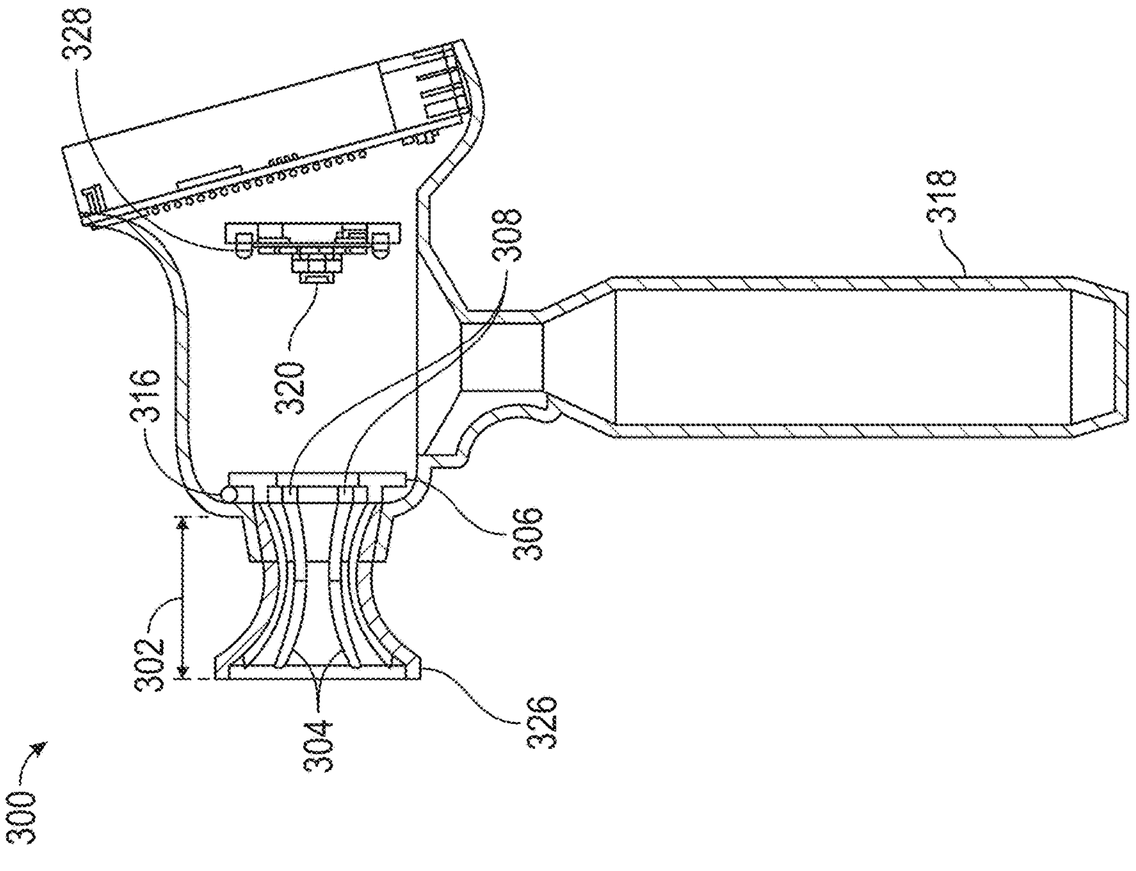
FIG. 3A is a schematic depiction of a second embodiment of the therapeutic device.

Referring to FIG. 3A, in some embodiments, a therapeutic device 300 includes an eye module 302 that includes an array of optical fibers 304. In some embodiments, the eye module can be connected to a housing 318 of the therapeutic device 300 through an eye module adapter 316. In some embodiments, the eye module adapter can be a mechanical interface to enable the eye module to be connected to the housing. In some embodiments, the housing can also include a camera module 320 and a non-ultraviolet light source 328, which correspond to the camera module and the non-ultraviolet light source of FIG. 2, with respect to structure and function. In some embodiments, a majority of the optical fibers, including all of the optical fibers, in the array of optical fibers can be configured to pass a corresponding and predetermined wavelength, angle, or intensity (or subset thereof, collectively spectral parameters) of ultraviolet light. In some embodiments, the array of optical fibers can be operatively connected to an ultraviolet light source 306. In some embodiments, the ultraviolet light source includes an array of ultraviolet light emitting diodes 308, an excimer lamp (not shown), a laser (not shown), or any combination thereof. In some embodiments, the ultraviolet light emitting diodes, among other components, can be configured to emit the ultraviolet light of a predetermined intensity, wavelength, and angle with respect to the eye module.

In some embodiments, the eye module can include an eye adapter 326 configured to support the array of optical fibers therein. Referring to FIG. 3B, providing a straight-on view of the eye adapter, in some embodiments, the eye adapter can be configured to enable ultraviolet light from the ultraviolet light source through array of optical fibers and non-ultraviolet light from the non-ultraviolet light source to exit through the eye adapter, which allowing the ultraviolet light and/or the non-ultraviolet light reflected from an eye of a subject to enter into the eye module through the eye adapter and received by the camera module.

Referring to FIG. 3C, the array of optical fibers 312 can include emitting portions 310 and an eye adapter interior surface 314. In some embodiments, the emitting portions of the array of optical fibers are mounted around the eye adapter interior surface of the eye module. In some embodiments, the emitting portion corresponds to an end of the array of optical fibers. In some embodiments, the emitting portion can be turned on or turned off, or moved relative to position of the eye of the subject to change intensity, wavelength, and/or angle of the ultraviolet light and/or the non-ultraviolet light. Since a majority or each optical fiber can emit ultraviolet light of predetermined spectral parameters, a first subset of optical fibers emitting ultraviolet light of desired spectral parameters can be turned on and a second subset of optical fibers emitting ultraviolet light of undesirable spectral parameters can be turned off when providing treatment to the subject, for example.

In some embodiments, the eye adapter interior surface can support the emitting portion. In some embodiments, the angle at which the ultraviolet light exits the eye adapter can be adjusted by moving the emitting portions along the eye module interior surface. In some embodiments, an eye module actuator (not shown) is operatively connected to the eye adapter, the emitting portions, or any combination thereof, of the therapeutic device 300. In some embodiments, the eye module actuator is configured to change an angle of incidence 322 of the ultraviolet light emitted from the emitting portions with respect to an eye 324 of the subject by moving the emitting portions along the eye module interior surface. In some embodiments, the eye module actuator is configured to change the angle of incidence from the emitting portions by moving the eye adapter toward or away from the eye, to rotate relatively to the eye, or any combination thereof.

Figure 4:
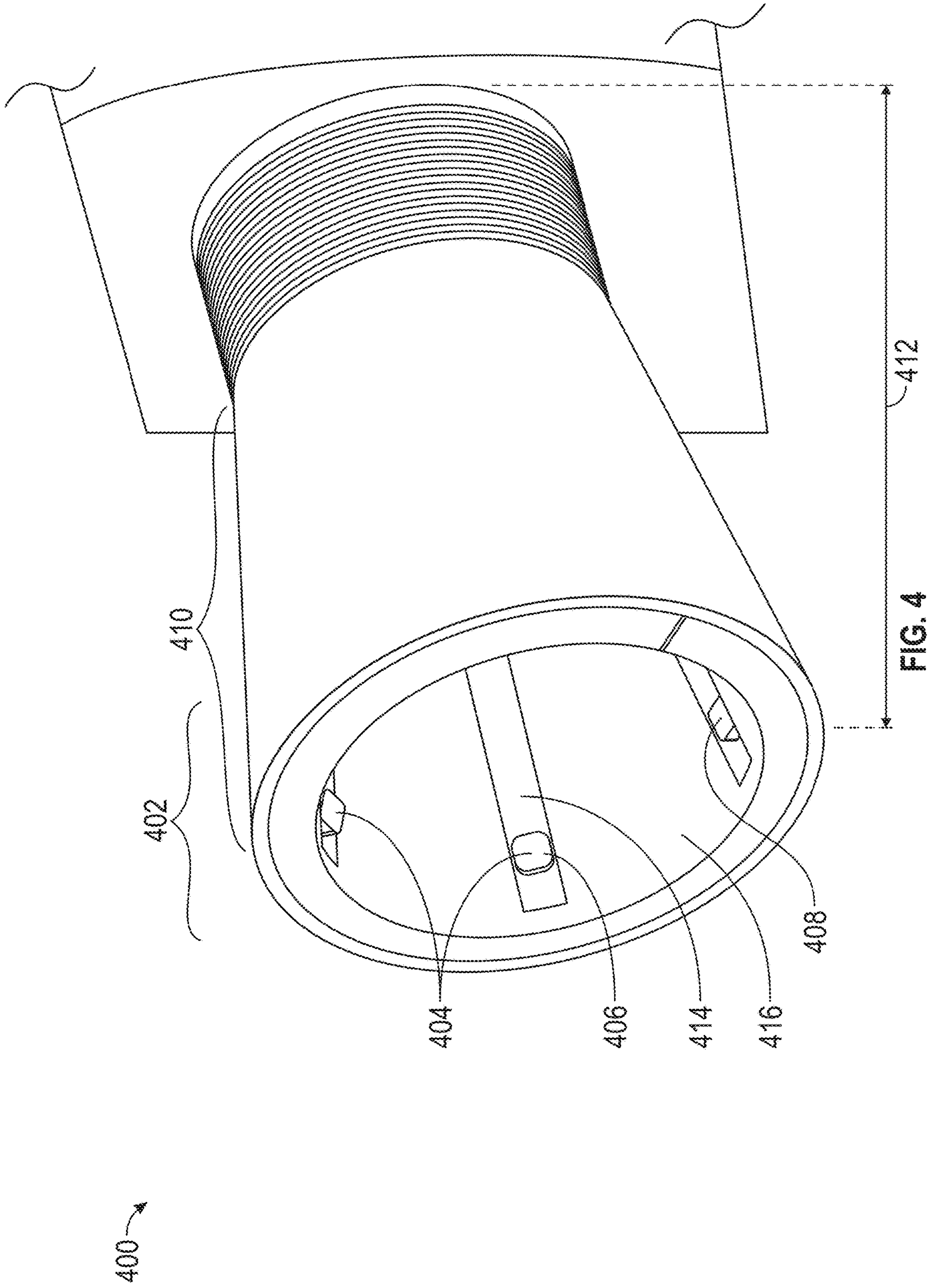
FIG. 4 is a schematic depiction of an embodiment of the therapeutic device having an array of UV sources mounted on actuator tracks along an eye module.

Referring to FIG. 4, a therapeutic device 400 includes an ultraviolet light source 402. The ultraviolet light source includes an array of ultraviolet light sources 404, such as light emitting diodes 406, 408 (first light emitting diode 406 and second light emitting diode 408) mounted on an actuator track 414 along an inner surface 416 of an eye module 412. In some embodiments, the light emitting diodes are configured to change the ultraviolet wavelength, the ultraviolet intensity, or the ultraviolet angle of incidence, or any combination thereof. In some embodiments, the ultraviolet light emitting diode is configured to change the ultraviolet angle of incidence by moving the ultraviolet light emitting diode along the actuator track. In some embodiments, two or more ultraviolet light emitting diodes are mounted on the actuator track, which are configured to change the ultraviolet wavelength, the ultraviolet intensity, or the ultraviolet angle of incidence, or any combination thereof, by turning on or off. In some embodiments, the actuator tracks can be located on an inner surface of an eye adapter 410 of an eye module. In some embodiments, the eye module can be reversibly attached to the therapeutic device 400 (or therapeutic devices 100, 200, 300), or to a fixed device such as a slit-lamp device.

Figure 5B:
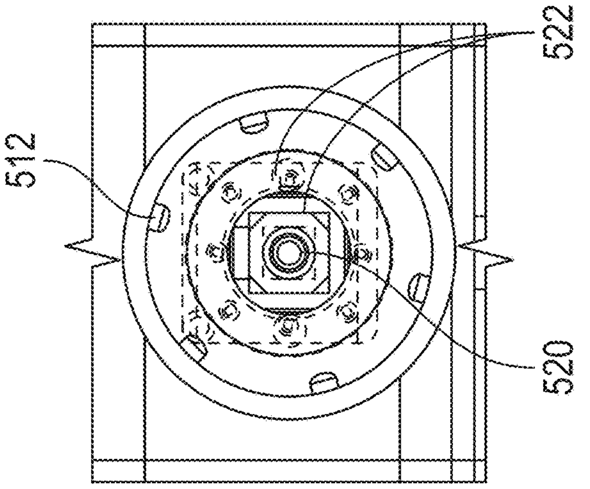
FIGS. 5A and 5B are schematic depictions of an embodiment of the therapeutic device having the array of UV sources positioned around the eye module at a plurality of angles.
Figure 5A:
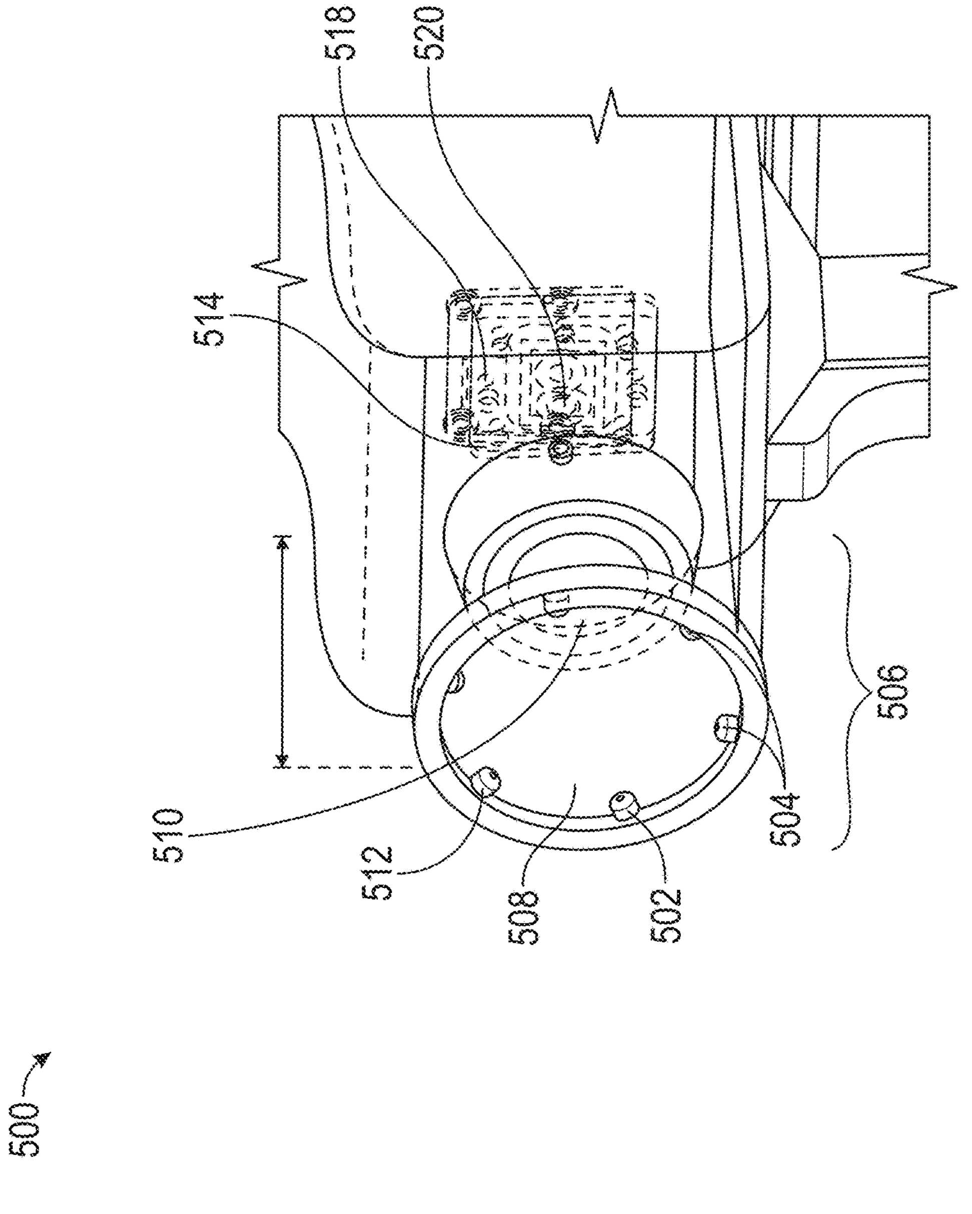

Referring to FIGS. 5A and 5B, in some embodiments, a therapeutic device 500 includes an eye adapter 506 of an eye module that supports an array of ultraviolet light emitting diodes 504 on an interior surface 508 thereof. In some embodiments, the array of ultraviolet light emitting diodes can also include a first UV LED 502 and a second UV LED 512, wherein the first and second UV LEDs (light emitting diode(s)) can be the same or different. In some embodiments, a majority or each of the ultraviolet light emitting diodes are capable of providing a predetermined range or subset of ultraviolet wavelengths, intensities, and angles. In such embodiments, the spectral parameters of the ultraviolet light emitted out from the eye module can be selected by turning on and turning off different subsets of UV LEDs in the array of ultraviolet light emitting diodes.

In some embodiments, the therapeutic device 500 includes a camera lens 520 associated with a camera module, located near a light source opening 510 of the therapeutic device 500. In some embodiments, the therapeutic device 500 includes a non-ultraviolet light source located near or adjacent to the camera lens. In some embodiments, the non-ultraviolet light source can include visible light emitting diode 512 or an infrared light emitting diode 514, or an array of visible light emitting diodes and infrared light emitting diodes 522, or any combination thereof. In some embodiments, visible light and infrared light are emitted by the infrared light source and the visible light source, 518, respectively. In some embodiments, the light source opening can be configured to allow the ultraviolet light or the non-ultraviolet light to exit the eye module, and also allow the ultraviolet light or the non-ultraviolet light reflected from the eye to be received by the camera lens through the light source opening.

Figure 6:
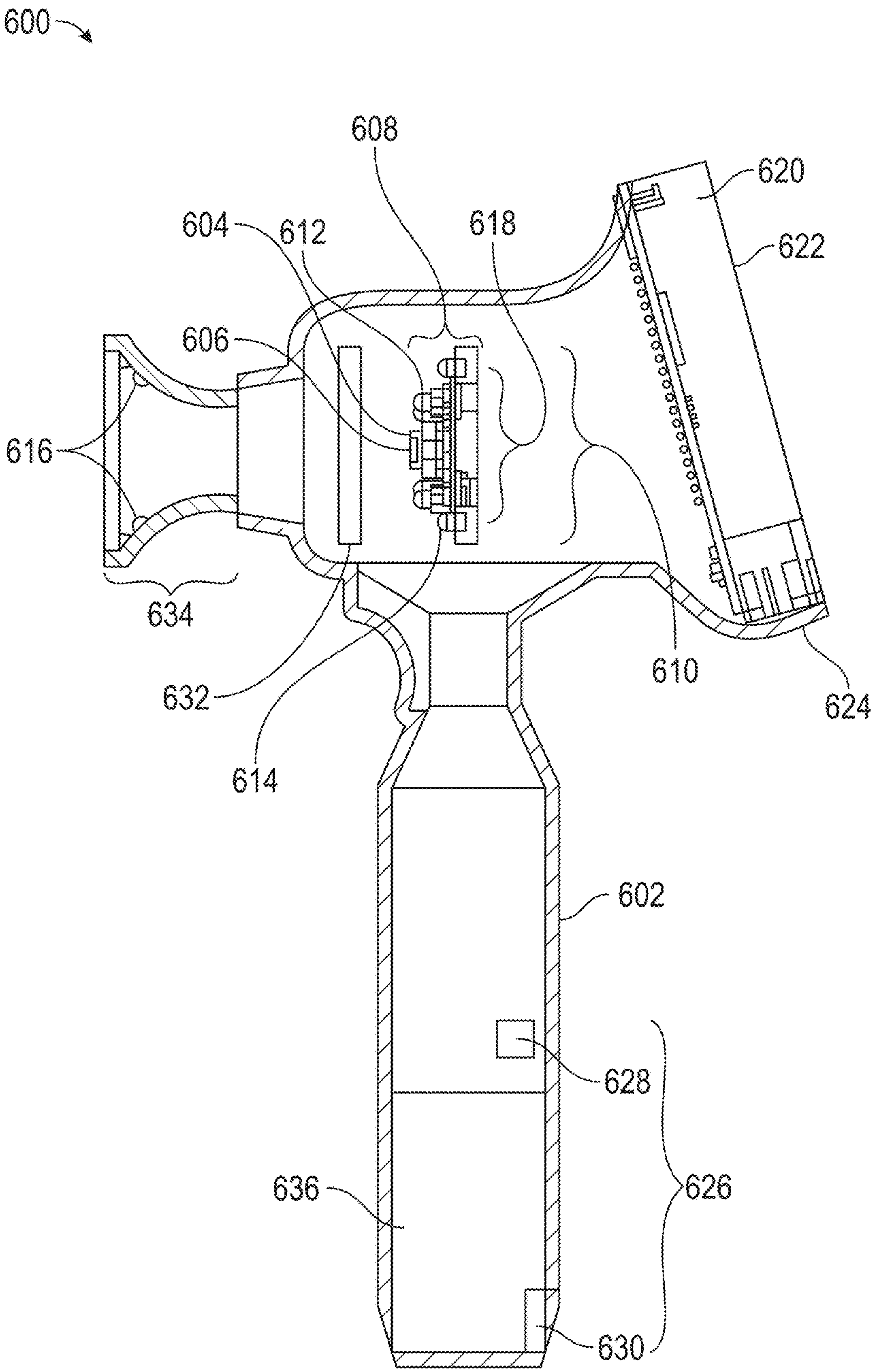
FIG. 6 is a schematic depiction of a cross-section of the therapeutic device having a processor, control panel, and data ports.

Referring to FIG. 6, in some embodiments, therapeutic device 600 includes a processor. In some embodiments, the therapeutic device 600 includes a housing 602 that retains the processor, among other components, therein. In some embodiments, the processor is operatively connected to an ultraviolet light source (not shown), a non-ultraviolet light source 610, a camera module 608, and an eye module 634. In some embodiments, the processor is configured to change the ultraviolet wavelength, the ultraviolet intensity, the ultraviolet angle of incidence, or any combination thereof, during an adjustment duration of from about 0.1 second to about 2.0 minutes by executing a computer readable code. In some embodiments, the processor is configured to be operatively connected to a control panel 622 or a touchscreen 620 located on the exterior 624 of the device 600. In some embodiments, the control panel or the touchscreen, the processor, and the data port can be implemented on a device circuit board. In some embodiments, the control panel can enable medical professionals to manually control the device 600, to visually inspect the eye of the subject, including the site of infection. In some embodiments, the processor is operatively connected to at least one communication link 626, which can include a short-range wireless connection 628, a universal serial bus (USB) connection (such as USB data port and power port 630), or a data port, or a combination thereof. In some embodiments, the short-range wireless connection enables the therapeutic device 600 to be controlled remotely by an external computing device. In some embodiments, the short-range wireless connection can be known communication technologies and networks including but not limited to a wireless-fidelity (Wi-Fi) network and a Bluetooth® network. Examples of the external computing device include smartphones, cell-phones, desktop computers, and the like. In some embodiments, the processor can communicate with a database of infections to use computer readable code, such as artificial intelligence, to diagnose the data collected from the camera module to determine and diagnose the infection. In some embodiments, the processor can use the diagnosis to change the angle, intensity, and or wavelength (UV spectral properties) directed toward the site of infection during treatment.

In some embodiments, the camera module includes a charged coupled device or a complementary metal oxide semiconductor (CMOS) image sensor. In some embodiments, the camera lens of the camera module is configured to focus light at a distance of from about 3.0 cm to about 25.0 cm from a surface of the camera lens. In some embodiments, the camera module includes a light transparent protective cover 632 between a surface of the camera lens and the eye module. In some embodiments, an array of visible light emitting diodes 618 and an infrared light emitting diode 614 is located near the camera module, surrounding the lens of the camera module. In some embodiments, a light transparent protector cover can be disposed between the eye module and the camera module. In some embodiments, the processor can also be configured to sample data from the camera module to determine locations of infections and corresponding treatments based on data received from the camera module.

In some embodiments, the housing contains a camera module opening 604 surrounding a lens 606 of the camera module 608. In some embodiments, the non-ultraviolet light source can include an array of infra-red light emitting diodes (which includes an infrared light emitting diode) on the camera module, visible light emitting diode 612 on the camera module, and another array of infrared light emitting diodes 616 at the eye module. In some embodiments, the visible light emitting diode is capable of emitting light at a visible wavelength of from about 400 nm to about 700 nm. In some embodiments, the infrared light emitting diode 614 capable of emitting an infrared light at a wavelength of from about 780 nm to about 1,000 nm. In some embodiments, the non-ultraviolet light source is located adjacent to a lens of the camera module. In some embodiments, the non-ultraviolet light source includes an array of visible light emitting diodes adjacent to or round a lens of the camera module. In some embodiments, the non-ultraviolet light source includes the array of infrared light emitting diodes adjacent to or round the lens of the camera module. In some embodiments, the housing can also include a battery 636 configured to supply power to the processor, the UV light source, and the non-UV light source, among other components.

Figure 7:
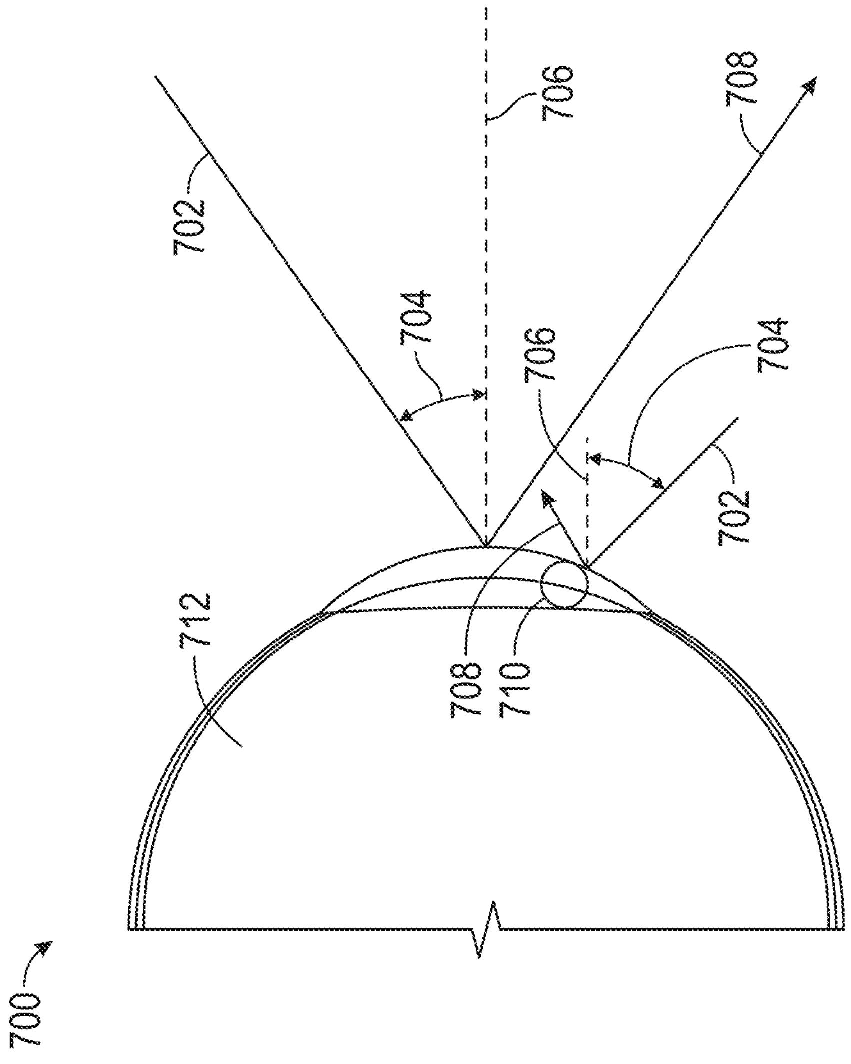
FIG. 7 is a schematic depiction of an angle of incidence of the UV light defined relative to a central axis passing through a center of a light source opening.

Referring to representation 700 if of FIG. 7, in some embodiments, an angle of incidence 704 of the ultraviolet light 702 is located relative to a central axis 706 passing through the center of a light source opening/eye module of a therapeutic device (e.g., 100, 200, 300, 400, 500, and 600), to the center of a camera lens. The angle of incidence is the angle that the incoming ultraviolet light makes relative to the central axis. Further, the ultraviolet light can reflect off the surface of an eye 712 of the subject as reflected light 708. In some embodiments, when an infection 710 is on a side portion of the eye, angle of incidence can be changed to direct the ultraviolet light towards the infection, while causing the reflected light to be directed towards the camera module. However, it can be appreciated by skilled artisans that an infection can be treat-able with multiple angles of incidences, and accordingly the ultraviolet light can be directed toward multiple inflection points simultaneously or in sequence.

Figure 8A:
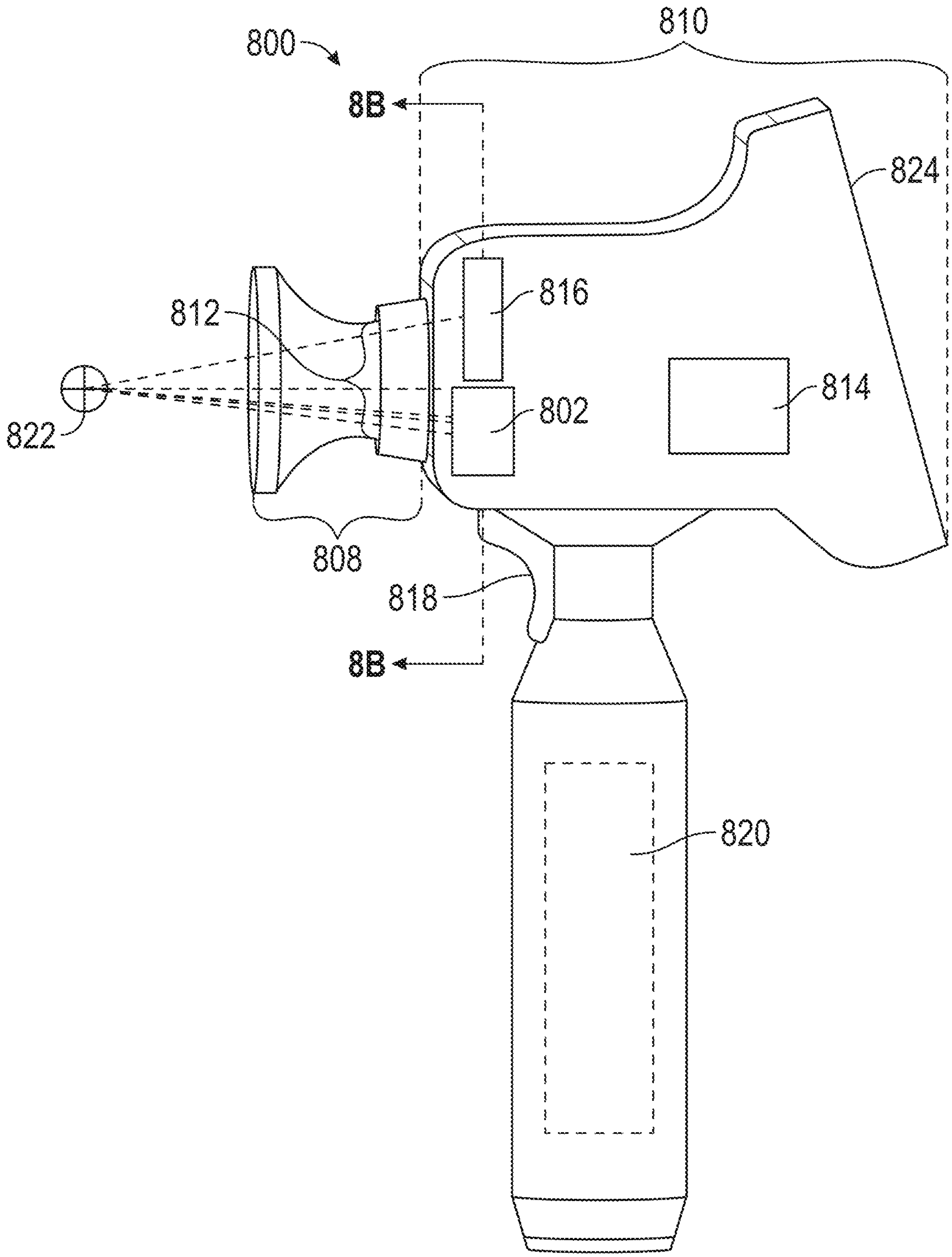
FIG. 8A is a schematic depiction of an embodiment of the therapeutic device having an array of UV sources and non-UV sources mounted within the device housing and configured to direct light toward an eye or light source opening.
Figure 8B:
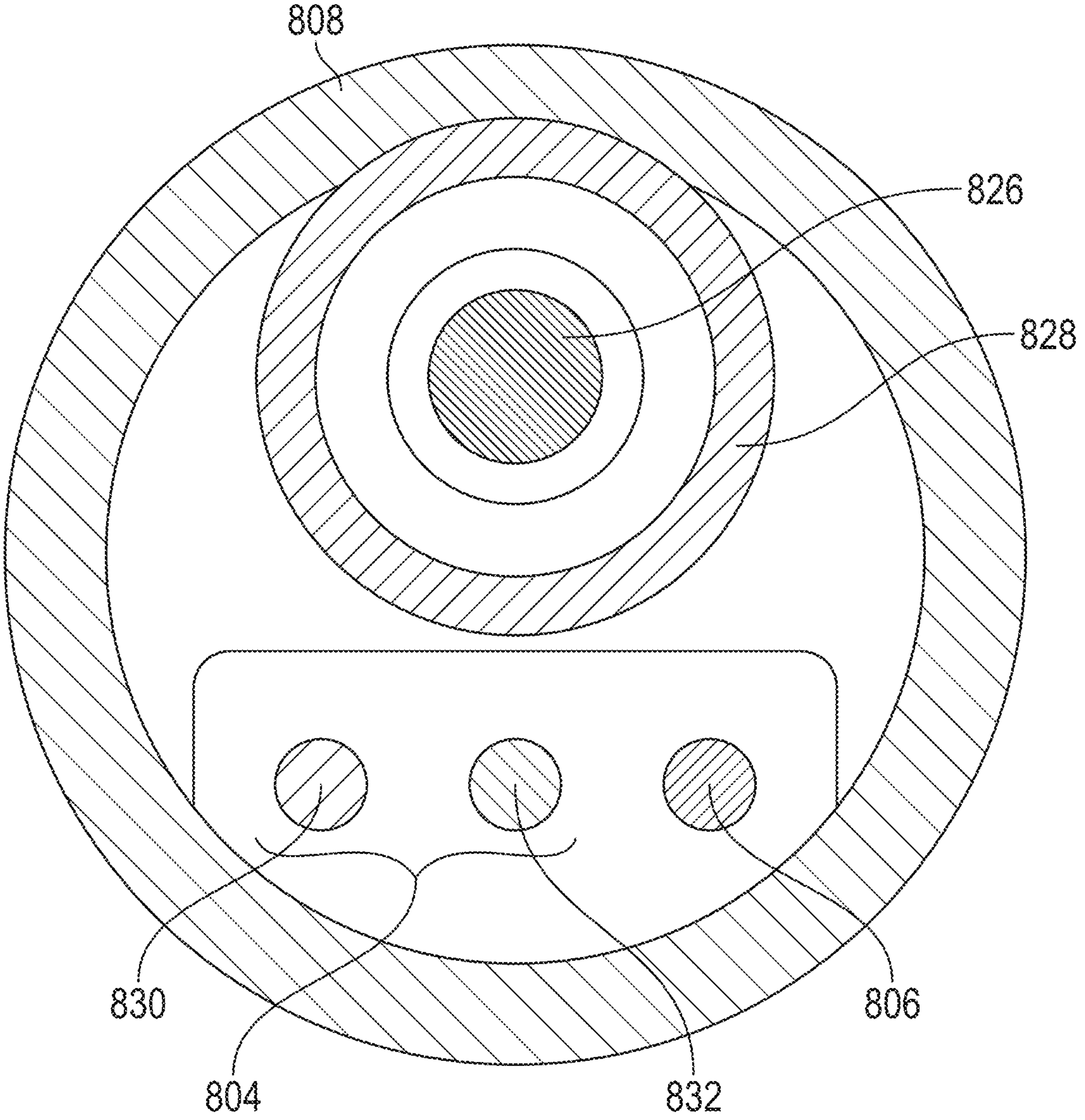
FIG. 8B is a schematic depiction of an embodiment of the therapeutic device from FIG. 8A, showing a front view of the therapeutic device looking into the eye module.

Referring to FIGS. 8A and 8B, in the embodiment shown, as in previous embodiments shown above, the therapeutic device includes a processor 814, a camera 816, a trigger 818, a battery 820, and a display screen 824. In the embodiment of the therapeutic device 800 shown, the ultraviolet light source 802 includes an array of ultraviolet light emitting diodes 804 and a non-ultraviolet light source 806 mounted within the housing 810 and directed toward the light source opening 812 and through the eye module 808 toward a target eye 822. Referring to FIG. 8B, in the embodiment shown, a ring light 828 surrounds the camera lens 826, providing additional UV or non-UV light for illuminating the target eye.

In practice, the subject would look into eye module and toward the array of ultraviolet light emitting diodes 804, wherein the array of ultraviolet light emitting diodes includes a first light emitting diode 830 and a second light emitting diode 832, wherein the first and second light emitting diodes can emit the same or different wavelength of UV light, the same or different intensity of UV light, or both. In this embodiment, the wavelength of UV light, the intensity of UV light, or the angle of UV light emitted from the array of UV light sources can be varied by turning on or off the first light emitting diode and the second light emitting diode separately or in combination. In some embodiments, the array of light emitting diodes includes 3 or more light emitting diodes which can be turned on or off to change the wavelength of UV light, the intensity of UV light, or the angle of UV light emitted from the array of UV light sources during operation.

Method

Embodiments of a method of treating a corneal abrasion, a corneal infection, or both, in a subject in need thereof are disclosed. In some embodiments, the method includes providing a therapeutic device, where the therapeutic device includes a housing including an eye module; a camera module mounted in the housing and configured to detect light from the eye module; a non-ultraviolet light source configured to direct non-ultraviolet light through the eye module; and an ultraviolet light source configured to direct ultraviolet light through the eye module at an ultraviolet wavelength, an ultraviolet intensity, and an ultraviolet angle of incidence. In some embodiments, the ultraviolet light source is configured to change the ultraviolet wavelength within an ultraviolet range of from about 200 nm to about 300 nm, to change the ultraviolet intensity within an ultraviolet intensity range of from about 2.0 mJ/cm$^2$ to about 1,500 mJ/cm$^2$, and/or to change the ultraviolet angle of incidence within an ultraviolet angle range of from 0° to 90°. In some embodiments, the method further includes directing the ultraviolet light into the eye of the subject at the ultraviolet wavelength, the ultraviolet intensity, and/or the ultraviolet angle of incidence for a therapeutic duration.

In some embodiments, the therapeutic duration is or can be from about 1.0 second to about 5.0 minutes. In some embodiments, the method further comprises, changing the ultraviolet wavelength, the ultraviolet intensity, and/or the ultraviolet angle of incidence, during an adjustment duration of from about 0.1 second to about 2.0 minutes before, during, or after the therapeutic duration. In some embodiments, the subject is a human being or a mammal.

In some embodiments, before, during, or after directing the ultraviolet light into the eye of the subject, the method further comprises directing the non-ultraviolet light into the eye of the subject. In some embodiments, the method further comprises locating an infection area of the eye of the subject and directing the ultraviolet light onto the infection area. In some embodiments, the method further comprises locating an infection area of the eye of the subject by directing the non-ultraviolet light into the eye of the subject and changing the ultraviolet wavelength, the ultraviolet intensity, and/or the ultraviolet angle of incidence.

In some embodiments, the housing contains a processor that is operatively connected to the ultraviolet light source, the non-ultraviolet light source, the camera module, and/or the eye module, and the method includes changing the ultraviolet wavelength, the ultraviolet intensity, and/or the ultraviolet angle of incidence, during an adjustment duration of from about 0.10 second to about 2.0 minutes by executing a machine-readable code. In some embodiments, the housing contains a processor, that is operatively connected to the ultraviolet light source, the non-ultraviolet light source, the camera module, and/or the eye module. In such embodiments, the method further includes changing the ultraviolet wavelength, the ultraviolet intensity, and/or the ultraviolet angle of incidence, during an adjustment duration of from about 0.1 seconds to about 2.0 minutes by transmitting a signal from the processor to an actuator, where the actuator is operatively connected to the ultraviolet light source, the non-ultraviolet light source, the camera module, and/or the eye module.

In some embodiments, the housing contains a processor, and the method includes diagnosing the corneal infection by directing the non-ultraviolet light into the eye of the subject, detecting a reflected light from the eye of the subject in the camera module, gathering reflected light data by measuring a reflected wavelength, a reflected intensity, and a reflected light position within an area of the eye of the subject, comparing the reflected light data to a database of corneal infections, and forming a diagnosis by comparing the reflected light data to a type of corneal infection. In some embodiments, the method further includes forming an infection area data map of the eye by comparing the reflected light data to normal eye data, a database of corneal infections, or both.

In some embodiments, after forming the diagnosis, the method further includes changing the ultraviolet wavelength, the ultraviolet intensity, and/or the ultraviolet angle of incidence based on the reflected light data, the type of corneal infection, or both. In some embodiments, after forming the infection area map, the method further includes directing from about 50% to 100% of the ultraviolet light onto a mapped infection area of the eye of the subject, where the mapped infection area of the eye corresponds to or matches the infection area data map.

EXAMPLES AND APPLICATIONS

In some embodiments, the therapeutic devices (e.g., 100 to 600) can be implemented either as handheld devices, or as attachments to eye treatment platform. In some embodiments, the eye adapter can be reversibly attachable, such that different eye adapters could be provided for different subjects (human or an animal) and different scenarios. In some embodiments, either one, two, or more of the eye modules (such as 104, 214, 302, 412, and 634) can be included in the therapeutic devices to enable both or all eyes of one or multiple subjects to be treated at once, simultaneously or in succession. Multiple eye modules can be adapted to have different specifications, thereby enhancing versatility of the device.

As stated, the eye module, or the eye adapter thereof, can have different geometric profiles and dimensions. In some embodiments, the raised lip has a lip diameter or a lip longest distance across the eye adapter of from about 40.0 mm to about 60.0 mm, including from about 42.0 mm to about 57.0 mm, including from about 38.0 mm to about 54.0 mm. In some embodiments, the lip diameter is from about 48.0 mm to about 51.0 mm. Further, in some embodiments, the eye adapter recess has an eye adapter depth of about 1.0 cm to about 5.0 cm from the raised lip to the light source opening, from about 1.5 cm to about 4.5 cm, including from about 2.0 cm to about 4.0 cm. In some embodiments, the eye adapter depth is about 3.0 cm. The dimensions can be selected based on requirements and constraints of the situation. In some embodiments, the dimensions can be adapted based on whether the subject is human or animal.

Further, as stated, different ultraviolet light sources can be used in the therapeutic device. In some embodiments, the UV light source includes at least one light source selected from the group including: an array of light emitting diodes capable of emitting ultraviolet light, a deuterium arc lamp, a xenon arc lamp, a laser, an excimer, and a combination thereof, but not limited thereto. In some embodiments, the ultraviolet light source is configured to change the ultraviolet wavelength within an ultraviolet range of from about 200 nm to about 300 nm, including from about 205 nm to about 295 nm, including from about 210 nm to about 290 nm. In some embodiments, the ultraviolet wavelength is about 235 nm, which corresponds to a wavelength at which absorption by genetic structures of infectious microorganisms, such as deoxyribonucleic acid (DNA) and ribonucleic acid (RNA), occurs maximally, making it particularly effective for disinfection. Furthermore, the ultraviolet light source can be configured to change the ultraviolet intensity within an ultraviolet intensity range of from about 2.0 $mJ/cm^2$ to about 1,500 $mJ/cm^2$, including from about 10 $mJ/cm^2$ to about 1,000 $mJ/cm^2$, including from about 10 $mJ/cm^2$ to about 150 $mJ/cm^2$. In some embodiments, the ultraviolet light source is configured to change the ultraviolet angle of incidence within an ultraviolet angle range of from 0° to 90°, including from about 10° to about 80°, including from about 20° to about 70°. In some embodiments, the spectral parameters of the ultraviolet light can be selected based on efficacy thereof for treatment.

The therapeutic device can include various actuators for moving the ultraviolet light sources or optical fibers to dynamically adjust the spectral parameters of the UV light. In some embodiments, the actuators include, but are not limited to, piezoelectric actuators, shape memory alloys, electromagnetic actuators, or microfluidic actuators, stepper motors, servo motors, or combinations thereof. In some embodiments, the actuators can control the position and movement of the ultraviolet light emitting components, thereby enabling fine adjustments to the treatment parameters. In some embodiments, the actuators can be controlled by the processor, which can process data collected by the camera module to determine the change required to the spectral parameters.

Further, in some embodiments, the camera module, such as 226, 320, and 608, can comprise a charged coupled device (CCD) or a complementary metal oxide semiconductor (CMOS) image sensor. In some embodiments, the camera module further includes a camera lens configured to focus light at a distance of from about 3.0 cm to about 25.0 cm from a surface of the camera lens, including from about 5.0 cm to about 20 cm, including from about 8.0 cm to about 15 cm. In some embodiments, the camera lens is configured to focus light at a distance of about 10 cm. In some embodiments, the camera module can include a light transparent protective cover between a surface of the camera lens and the eye module.

In some embodiments, the device has a device weight of about 227.0 g to about 1,360.0 g, including from about 300.0 g to about 1,200.0 g, including about 400.0 g to about 1 kg. In some embodiments, the device weight is about 700.0 g. In some embodiments, the therapeutic duration is from about 1.0 second to about 5.0 minutes, including from about 5 seconds to about 4 minutes, including from about 10 seconds to about 3 minutes. In some embodiments, the therapeutic duration is about 1 minute. In some embodiments, the adjustment duration is from about 0.1 second to about 2.0 minutes, including from about 0.2 seconds to about 1.5 minutes, including from about 0.5 seconds to about 1.0 minute. In some embodiments, the adjustment duration is about 30 seconds.

In some embodiments, the housing contains actuator adjustable focal lens, a frequency doubler, an aperture, or any combination thereof. In some embodiments, the frequency doubler converts visible or infrared light (from the non-ultraviolet light source) to ultraviolet light. In some embodiments, the frequency doublers can include, but are not limited to, potassium dihydrogen phosphate (KDP) crystals, beta barium borate (BBO) crystals, and lithium triborate (LBO) crystals. In some embodiments, the aperture limits, reduces, minimizes, varies, changes, or adjusts the amount of ultraviolet or non-ultraviolet light that passes through. In some embodiments, the actuator adjustable focal lens limits, reduces, minimizes, varies, changes, or adjusts a focal length for the ultraviolet or non-ultraviolet light. In some embodiments, the camera lens of the camera module is configured to focus light at a distance of from about 3.0 cm to about 25.0 cm from a surface of the camera lens, including from about 5 cm to about 20 cm, including from about 7 cm to about 17 cm. In some embodiments, the camera lens is configured to focus light at a distance of about 10 cm.

In some embodiments, the processor is configured to change the ultraviolet wavelength, the ultraviolet intensity, the ultraviolet angle of incidence, or any combination thereof, during an adjustment duration of from about 0.1 second to about 2.0 minutes by executing a computer readable code, including from about 0.2 seconds to about 1.5 minutes, including from about 0.5 seconds to about 1 minute. In some embodiments, the computer readable code includes a software program, a set of instructions, or an algorithm that controls the operation of the UV light source and other components of the device.

The therapeutic device can also include non-ultraviolet light sources, for aligning the eye and locating wounded and infected portions thereover, as well as providing therapeutic benefit of infrared light to reduce inflammation. The non-ultraviolet light sources can include visible light emitting diodes and infrared light emitting diodes. In some embodiments, the visible light emitting diode is capable of emitting light at a visible wavelength of from about 400 nm to about 700 nm; including from about 420 nm to about 680 nm, including from about 450 nm to about 650 nm. In some embodiments, the infrared light emitting diode is capable of emitting an infrared light at a wavelength of from about 780 nm to about 1,000 nm; including from about 800 nm to about 980 nm, including from about 820 nm to about 950 nm. In some embodiments, the infrared light emitting diode is capable of emitting infrared light at a wavelength of about 900 nm. A benefit of the devices and methods disclosed herein can be the inclusion of visible and infrared light sources because the combination of these light sources can detect and map corneal abrasion. Further, the infrared light can provide an anti-inflammatory effect that prevents, ameliorate, and/or reduces the likelihood of morbid sequelae forming, such as such as immune-mediated reactions that lead to melting of the cornea and stroma.

In some embodiments, the therapeutic device collects and processes data for accurate diagnosis and personalized treatment. In some embodiments, the camera module, in conjunction with the non-ultraviolet light source, can gather data about the corneal abrasion, corneal infection, or both. In some embodiments, as the non-ultraviolet light illuminates the eye, the camera captures detailed images of the cornea. In some embodiments, these images are then processed by the processor of the therapeutic device, which can use, among other techniques or models, artificial intelligence modules, statistical models, expert systems, symbolic reasoning models, and the like, to identify and characterize the infection for diagnosis. In some embodiments, the collected data can include information about the size, shape, location, and light-scattering properties of the infected area. Such data can be helpful for determining the appropriate spectral parameters for the UV light, ensuring that the treatment is targeted and effective.

In some embodiments, the data collection and processing can be used for tracking the progression of the infection over time or over the course of the treatment, and provide insights into the delivered dosage of the treatment, allowing for data-driven adjustments to the spectral parameters of the UV light for optimized treatment outcomes. In some embodiments, therapeutic device can also be configured to securely store and transmit the collected data to a remote server or cloud platform for further analysis, research, personalization of treatment, and treatment monitoring. In some embodiments, the data collection and processing is performed in real-time, to obtain real-time feedback of the efficacy of the treatment. Further, the spectral parameters of the ultraviolet light can be changed based on the efficacy determined.

SOME DETAILED EMBODIMENTS

Embodiment 1. A therapeutic device for treating a corneal abrasion, a corneal infection, or prophylaxis of a corneal infection, or any combination thereof, comprising:

a housing including an eye module;

a camera module mounted in the housing and configured to detect light from the eye module;

a non-ultraviolet light source configured to direct non-ultraviolet light through the eye module; and an ultraviolet light source configured to direct ultraviolet light through the eye module at an ultraviolet wavelength, an ultraviolet intensity, and an ultraviolet angle of incidence, wherein the ultraviolet light source is configured to change the ultraviolet wavelength within an ultraviolet range of from about 200 nm to about 300 nm, to change the ultraviolet intensity within an ultraviolet intensity range of from about 2.0 mJ/cm2 to about 1,500 mJ/cm2, or to change the ultraviolet angle of incidence within an ultraviolet angle range of from 0° to 90°, or any combination thereof.

Embodiment 2. The therapeutic device of one or more of embodiments 1-8 or 15, wherein the eye module is located on an exterior of the housing and includes a light source opening surrounded by an eye adapter, wherein the eye adapter has a ring shape with a raised lip surrounding an eye adapter recess, wherein the eye adapter recess surrounds the light source opening; and wherein the raised lip has a lip diameter or a lip longest distance across the eye adapter of from about 40.0 mm to about 60.0 mm; or wherein the eye adapter recess has an eye adapter depth of about 1.0 cm to about 5.0 cm from the raised lip to the light source opening; or wherein the therapeutic device has a device weight of about 227.0 g to about 1,360.0 g.

Embodiment 3. The therapeutic device of one or more of embodiments 1-8 or 15, further comprising:

a UV mirror, wherein the UV mirror includes a dichroic mirror or a metal-containing mirror, wherein the ultraviolet light source includes an array of ultraviolet light emitting diodes, an excimer lamp, a laser, or a combination thereof;

wherein the UV mirror is configured to direct non-ultraviolet light from the non-ultraviolet light source through the eye module; or wherein the UV mirror is configured to direct the ultraviolet light from the ultraviolet light source through the eye module; or wherein the UV mirror is configured to simultaneously direct non-ultraviolet light from the non-ultraviolet light source and the ultraviolet light from the ultraviolet light source through the eye module; or wherein the UV mirror is located between the eye module and the camera module; or wherein the UV mirror is located between the eye module and the ultraviolet light source; or wherein the housing contains an actuator adjustable focal lens, a frequency doubler, a triple filter, one or more rotatable filters, a mechanically rotatable filter, or an aperture, or a combination thereof, located between the eye module and the ultraviolet light source, and one or more of the actuator adjustable focal lens, the frequency doubler, the triple filter, one or more rotatable filters, the mechanically rotatable filter, the aperture, or the combination thereof, are configured to change the ultraviolet wavelength, the ultraviolet intensity, or the ultraviolet angle of incidence, or any combination thereof; or wherein the housing contains an actuator a frequency doubler, a mechanically rotatable filter, or both, located between the eye module and the non-ultraviolet light source, and configured to convert the non-ultraviolet light into the ultraviolet light; or any combination thereof.

Embodiment 4. The therapeutic device of one or more of embodiments 1-8 or 15, wherein the eye module includes an array of optical fibers, wherein the array of optical fibers is operatively connected to the ultraviolet light source, wherein the ultraviolet light source includes an array of ultraviolet light emitting diodes, an excimer lamp, a laser, or a combination thereof;

wherein emitting portions of the array of optical fibers are mounted around an eye adapter interior surface of the eye module;

wherein an eye module actuator is operatively connected to the eye adapter, the emitting portions, or any combination thereof; and wherein the eye module actuator is configured to change the ultraviolet angle of incidence from the emitting portions by moving the emitting portions along the eye module interior surface; or wherein the eye module actuator is configured to change the ultraviolet angle of incidence from the emitting portions by moving the eye adapter; or wherein the eye module contains one or more movable reflectors capable of changing the angle of incidence relative to the emitting portions;

or any combination thereof.

Embodiment 5. The therapeutic device of one or more of embodiments 1-8 or 15, wherein the ultraviolet light source includes an array of ultraviolet light emitting diodes mounted around an eye adapter interior surface of the eye module, wherein an ultraviolet light emitting diode of the array of ultraviolet light emitting diodes is mounted on an actuator track, and wherein the ultraviolet light emitting diode is configured to change the ultraviolet angle of incidence by moving the ultraviolet light emitting diode along the actuator track; or wherein two or more ultraviolet light emitting diodes of the array of ultraviolet light emitting diodes are mounted on an actuator track, and the two or more ultraviolet light emitting diodes are configured to change the ultraviolet wavelength, the ultraviolet intensity, or the ultraviolet angle of incidence, or any combination thereof, by turning on or off.

Embodiment 6. The therapeutic device of one or more of embodiments 1-8 or 15, wherein the ultraviolet light source includes an array of ultraviolet light emitting diodes mounted around an eye adapter interior surface of the eye module, wherein two or more ultraviolet light emitting diodes of the array of ultraviolet light emitting diodes are configured to change the ultraviolet wavelength, the ultraviolet intensity, or the ultraviolet angle of incidence, or any combination thereof, by turning on or off.

Embodiment 7. The therapeutic device of one or more of embodiments 1-8 or 15, wherein the housing contains a camera module opening surrounding a lens of the camera module, and wherein the non-ultraviolet light source includes a visible light emitting diode, an infrared light emitting diode, an array of visible light emitting diodes, an array infrared light emitting diodes, or a combined array of visible light emitting diodes and infrared light emitting diodes, or any combination thereof; or wherein the non-ultraviolet light source includes a visible light emitting diode capable of emitting light at a visible wavelength of from about 400 nm to about 700 nm; or wherein the non-ultraviolet light source includes an infrared light emitting diode capable of emitting an infrared light at a wavelength of from about 780 nm to about 1,000 nm; or wherein the non-ultraviolet light source is located adjacent to a lens of the camera module; or wherein the non-ultraviolet light source includes an array of visible light emitting diodes adjacent to or round a lens of the camera module;

wherein the non-ultraviolet light source includes an array of infrared light emitting diodes adjacent to or round a lens of the camera module; or any combination thereof.

Embodiment 8. The therapeutic device of one or more of embodiments 1-8 or 15, wherein the housing contains a processor, wherein the processor is operatively connected to the ultraviolet light source, the non-ultraviolet light source, the camera module, or the eye module, or any combination thereof, and wherein the processor is configured to change the ultraviolet wavelength, the ultraviolet intensity, or the ultraviolet angle of incidence, or any combination thereof, during an adjustment duration of from about 0.1 second to about 2.0 minutes by executing a computer readable code; or wherein the housing contains a processor, wherein the processor is operatively connected to a control panel located on the device exterior, or wherein the processor is operatively connected to at least one communication link, or any combination thereof, wherein the communication link includes a short-range wireless connection, a universal serial bus (USB) connection, or a data port; or wherein the camera module includes a charged coupled device or a complementary metal oxide semiconductor (CMOS) image sensor; or a camera lens configured to focus light at a distance of from about 1.0 cm to about 25.0 cm from a surface of the camera lens; or the camera module includes a light transparent protective cover between a surface of the camera lens and the eye module; or wherein the housing contains the ultraviolet light source and the non-ultraviolet light source and one or both of the ultraviolet light source and the non-ultraviolet light source are configured to move along a track or to change ultraviolet intensity or both; or any combination thereof.

Embodiment 9. A method of detecting or treating a corneal abrasion, a corneal infection, or prophylaxis of a corneal infection, or any combination thereof, in a subject in need thereof, comprising:

providing a therapeutic device, wherein the therapeutic device includes, a housing including an eye module; a camera module mounted in the housing and configured to detect light from the eye module; a non-ultraviolet light source configured to direct non-ultraviolet light through the eye module; and an ultraviolet light source configured to direct ultraviolet light through the eye module at an ultraviolet wavelength, an ultraviolet intensity, and an ultraviolet angle of incidence, wherein the ultraviolet light source is configured to change the ultraviolet wavelength within an ultraviolet range of from about 200 nm to about 300 nm, to change the ultraviolet intensity within an ultraviolet intensity range of from about 2.0 mJ/cm2 to about 1,500 mJ/cm2, or to change the ultraviolet angle of incidence within an ultraviolet angle range of from 0° to 90°, or any combination thereof; and directing the ultraviolet light into the eye of the subject at the ultraviolet wavelength, the ultraviolet intensity, or the ultraviolet angle of incidence, or any combination thereof, for a therapeutic duration.

Embodiment 10. The method of one or more of embodiments 9-14, wherein the therapeutic duration is from about 1.0 second to about 5.0 minutes; or further comprising, changing the ultraviolet wavelength, the ultraviolet intensity, or the ultraviolet angle of incidence, or any combination thereof, during an adjustment duration of from about 0.1 second to about 2.0 minutes before, during, or after the therapeutic duration; or wherein the subject is a human being or a mammal.

Embodiment 11. The method of one or more of embodiments 9-14, further comprising:

before, during, or after directing the ultraviolet light into the eye of the subject, reducing inflammation or microbial burden; or treating a wound by directing the non-ultraviolet light, including infrared light, into the eye of the subject; or before or during directing the ultraviolet light into the eye of the subject, contacting the eye of the subject with hypochlorous acid;

locating an infection area of the eye of the subject and directing the ultraviolet light onto the infection area; or locating and mapping an infection area of the eye of the subject by directing the non-ultraviolet light into the eye of the subject and changing the ultraviolet wavelength, the ultraviolet intensity, or the ultraviolet angle of incidence, or any combination thereof; or wherein the housing contains a processor, wherein the processor is operatively connected to the ultraviolet light source, the non-ultraviolet light source, the camera module, or the eye module, or any combination thereof, and changing the ultraviolet wavelength, the ultraviolet intensity, or the ultraviolet angle of incidence, or any combination thereof, during an adjustment duration of from about 0.10 second to about 2.0 minutes by executing a machine-readable code; or wherein the housing contains a processor, wherein the processor is operatively connected to the ultraviolet light source, the non-ultraviolet light source, the camera module, or the eye module, or any combination thereof, and changing the ultraviolet wavelength, the ultraviolet intensity, or the ultraviolet angle of incidence, or any combination thereof, during an adjustment duration of from about 0.10 second to about 2.0 minutes by transmitting a signal from the processor to an actuator, wherein the actuator is operatively connected to the ultraviolet light source, the non-ultraviolet light source, the camera module, or the eye module, or any combination thereof.

Embodiment 12. The method of one or more of embodiments 9-14, wherein the housing contains a processor, diagnosing the corneal infection by;

directing the non-ultraviolet light into the eye of the subject, detecting a reflected light from the eye of the subject in the camera module, and gathering reflected light data by measuring a reflected wavelength, a reflected intensity, and a reflected light position within an area of the eye of the subject, comparing the reflected light data to a database of corneal infections; and forming a diagnosis by comparing the reflected light data to a type of corneal infection; or forming an infection area data map of the eye by comparing the reflected light data to normal eye data, a database of corneal infections, or both; or any combination thereof.

Embodiment 13. The method of one or more of embodiments 9-14, further comprising:

after forming the diagnosis, changing the ultraviolet wavelength, the ultraviolet intensity, or the ultraviolet angle of incidence, or any combination thereof, based on the reflected light data, the type of corneal infection, or both; or after forming the infection area map, directing from about 50% to 100% of the ultraviolet light onto a mapped infection area of the eye of the subject, wherein the mapped infection area of the eye corresponds to or matches the infection area data map; or any combination thereof.

Embodiment 14. The method of one or more of embodiments 9-14, further comprising:

before, during, or after directing the ultraviolet light into the eye of the subject, directing the non-ultraviolet light into the eye of the subject; or locating an abraded area of the eye of the subject and directing the ultraviolet light, infrared light, or both, onto the abraded area; or locating an abraded area of the eye of the subject by directing the non-ultraviolet light into the eye of the subject and changing the ultraviolet wavelength, the ultraviolet intensity, or the ultraviolet angle of incidence, the infrared wavelength, the infrared intensity, or the infrared angle of incidence, or any combination thereof; or wherein the housing contains a processor, wherein the processor is operatively connected to the ultraviolet light source, the non-ultraviolet light source, the camera module, or the eye module, or any combination thereof, and changing the ultraviolet wavelength, the ultraviolet intensity, or the ultraviolet angle of incidence, or any combination thereof, during an adjustment duration of from about 0.10 second to about 2.0 minutes by executing a machine-readable code; or wherein the housing contains a processor, wherein the processor is operatively connected to the ultraviolet light source, the non-ultraviolet light source, the camera module, or the eye module, or any combination thereof, and changing the ultraviolet wavelength, the ultraviolet intensity, or the ultraviolet angle of incidence, or any combination thereof, during an adjustment duration of from about 0.10 second to about 2.0 minutes by transmitting a signal from the processor to an actuator, wherein the actuator is operatively connected to the ultraviolet light source, the non-ultraviolet light source, the camera module, or the eye module, or any combination thereof.

Embodiment 15. The therapeutic device of one or more of embodiments 1-8 or 15, wherein the ultraviolet light source includes an array of ultraviolet light emitting diodes mounted around an eye adapter interior surface of the eye module, or mounted within the housing and directed toward the light source opening, or both; and wherein two or more ultraviolet light emitting diodes of the array of ultraviolet light emitting diodes are configured to change the ultraviolet wavelength, the ultraviolet intensity, or the ultraviolet angle of incidence, or any combination thereof, by turning on or off; or wherein the ultraviolet light source includes an array of ultraviolet light emitting diodes and a non-ultraviolet light source mounted around an eye adapter interior surface of the eye module, or mounted within the housing and directed toward the light source opening, or both; and wherein two or more ultraviolet light emitting diodes of the array of ultraviolet light emitting diodes are configured to change the ultraviolet wavelength, the ultraviolet intensity, or the ultraviolet angle of incidence, or any combination thereof, by turning on or off.

MORE DETAILED EMBODIMENTS

Embodiment 21. A therapeutic device for treating a corneal abrasion, a corneal infection, or prophylaxis of a corneal infection, or any combination thereof, comprising:

a housing including an eye module;

a camera module mounted in the housing and configured to detect light from the eye module;

a non-ultraviolet light source configured to direct non-ultraviolet light through the eye module; and an ultraviolet light source configured to direct ultraviolet light through the eye module at an ultraviolet wavelength, an ultraviolet intensity, and an ultraviolet angle of incidence, wherein the ultraviolet light source is configured to change the ultraviolet wavelength within an ultraviolet range of from about 200 nm to about 300 nm, to change the ultraviolet intensity within an ultraviolet intensity range of from about 2.0 mJ/cm2 to about 1,500 mJ/cm2, or to change the ultraviolet angle of incidence within an ultraviolet angle range of from 0° to 90°, or any combination thereof.

Embodiment 22. The therapeutic device of one or more of embodiments 21-28, wherein the eye module is located on an exterior of the housing and includes a light source opening surrounded by an eye adapter, wherein the eye adapter has a ring shape with a raised lip surrounding an eye adapter recess, wherein the eye adapter recess surrounds the light source opening; and wherein the raised lip has a lip diameter or a lip longest distance across the eye adapter of from about 40.0 mm to about 60.0 mm; or wherein the eye adapter recess has an eye adapter depth of about 1.0 cm to about 5.0 cm from the raised lip to the light source opening; or wherein the therapeutic device has a device weight of about 227.0 g to about 1,360.0 g.

Embodiment 23. The therapeutic device of one or more of embodiments 21-28, further comprising:

a dichroic mirror, wherein the ultraviolet light source includes an array of ultraviolet light emitting diodes, an excimer lamp, a laser, or a combination thereof;

wherein the dichroic mirror is configured to direct non-ultraviolet light from the non-ultraviolet light source through the eye module; or wherein the dichroic mirror is configured to direct the ultraviolet light from the ultraviolet light source through the eye module; or wherein the dichroic mirror is configured to simultaneously direct non-ultraviolet light from the non-ultraviolet light source and the ultraviolet light from the ultraviolet light source through the eye module; or wherein the dichroic mirror is located between the eye module and the camera module; or wherein the dichroic mirror is located between the eye module and the ultraviolet light source; or wherein the housing contains an actuator adjustable focal lens, a frequency doubler, a mechanically rotatable filter, or an aperture, or a combination thereof, located between the eye module and the ultraviolet light source, and one or more of the actuator adjustable focal lens, the frequency doubler, the mechanically rotatable filter, the aperture, or the combination thereof, are configured to change the ultraviolet wavelength, the ultraviolet intensity, or the ultraviolet angle of incidence, or any combination thereof; or wherein the housing contains an actuator a frequency doubler, a mechanically rotatable filter, or both, located between the eye module and the non-ultraviolet light source, and configured to convert the non-ultraviolet light into the ultraviolet light; or any combination thereof.

Embodiment 24. The therapeutic device of one or more of embodiments 21-28, wherein the eye module includes an array of optical fibers, wherein the array of optical fibers is operatively connected to the ultraviolet light source, wherein the ultraviolet light source includes an array of ultraviolet light emitting diodes, an excimer lamp, a laser, or a combination thereof;

wherein emitting portions of the array of optical fibers are mounted around an eye adapter interior surface of the eye module;

wherein an eye module actuator is operatively connected to the eye adapter, the emitting portions, or any combination thereof; and wherein the eye module actuator is configured to change the ultraviolet angle of incidence from the emitting portions by moving the emitting portions along the eye module interior surface; or wherein the eye module actuator is configured to change the ultraviolet angle of incidence from the emitting portions by moving the eye adapter; or any combination thereof.

Embodiment 25. The therapeutic device of one or more of embodiments 21-28, wherein the ultraviolet light source includes an array of ultraviolet light emitting diodes mounted around an eye adapter interior surface of the eye module, wherein an ultraviolet light emitting diode of the array of ultraviolet light emitting diodes is mounted on an actuator track, and wherein the ultraviolet light emitting diode is configured to change the ultraviolet angle of incidence by moving the ultraviolet light emitting diode along the actuator track; or wherein two or more ultraviolet light emitting diodes of the array of ultraviolet light emitting diodes are mounted on an actuator track, and the two or more ultraviolet light emitting diodes are configured to change the ultraviolet wavelength, the ultraviolet intensity, or the ultraviolet angle of incidence, or any combination thereof, by turning on or off.

Embodiment 26. The therapeutic device of one or more of embodiments 21-28, wherein the ultraviolet light source includes an array of ultraviolet light emitting diodes mounted around an eye adapter interior surface of the eye module, wherein two or more ultraviolet light emitting diode of the array of ultraviolet light emitting diodes are configured to change the ultraviolet wavelength, the ultraviolet intensity, or the ultraviolet angle of incidence, or any combination thereof, by turning on or off.

Embodiment 27. The therapeutic device of one or more of embodiments 21-28, wherein the housing contains a camera module opening surrounding a lens of the camera module, and wherein the non-ultraviolet light source includes a visible light emitting diode, an infrared light emitting diode, an array of visible light emitting diodes, an array infrared light emitting diodes, or a combined array of visible light emitting diodes and infrared light emitting diodes, or any combination thereof; or wherein the non-ultraviolet light source includes a visible light emitting diode capable of emitting light at a visible wavelength of from about 400 nm to about 700 nm; or wherein the non-ultraviolet light source includes an infrared light emitting diode capable of emitting an infrared light at a wavelength of from about 780 nm to about 1,000 nm; or wherein the non-ultraviolet light source is located adjacent to a lens of the camera module; or wherein the non-ultraviolet light source includes an array of visible light emitting diodes adjacent to or round a lens of the camera module;

wherein the non-ultraviolet light source includes an array of infrared light emitting diodes adjacent to or round a lens of the camera module; or any combination thereof.

Embodiment 28. The therapeutic device of one or more of embodiments 21-28, wherein the housing contains a processor, wherein the processor is operatively connected to the ultraviolet light source, the non-ultraviolet light source, the camera module, or the eye module, or any combination thereof, and wherein the processor is configured to change the ultraviolet wavelength, the ultraviolet intensity, or the ultraviolet angle of incidence, or any combination thereof, during an adjustment duration of from about 0.1 second to about 2.0 minutes by executing a computer readable code; or wherein the housing contains a processor, wherein the processor is operatively connected to a control panel located on the device exterior, or wherein the processor is operatively connected to at least one communication link, or any combination thereof, wherein the communication link includes a short-range wireless connection, a universal serial bus (USB) connection, or a data port; or wherein the camera module includes a charged coupled device or a complementary metal oxide semiconductor (CMOS) image sensor; or a camera lens configured to focus light at a distance of from about 3.0 cm to about 25.0 cm from a surface of the camera lens; or the camera module includes a light transparent protective cover between a surface of the camera lens and the eye module; or any combination thereof.

Embodiment 29. A method of treating a corneal abrasion, a corneal infection, or prophylaxis of a corneal infection, or any combination thereof, in a subject in need thereof, comprising:

providing a therapeutic device, wherein the therapeutic device includes, a housing including an eye module; a camera module mounted in the housing and configured to detect light from the eye module; a non-ultraviolet light source configured to direct non-ultraviolet light through the eye module; and an ultraviolet light source configured to direct ultraviolet light through the eye module at an ultraviolet wavelength, an ultraviolet intensity, and an ultraviolet angle of incidence, wherein the ultraviolet light source is configured to change the ultraviolet wavelength within an ultraviolet range of from about 200 nm to about 300 nm, to change the ultraviolet intensity within an ultraviolet intensity range of from about 2.0 mJ/cm2 to about 1,500 mJ/cm2, or to change the ultraviolet angle of incidence within an ultraviolet angle range of from 0° to 90°, or any combination thereof; and directing the ultraviolet light into the eye of the subject at the ultraviolet wavelength, the ultraviolet intensity, or the ultraviolet angle of incidence, or any combination thereof, for a therapeutic duration.

Embodiment 30. The method of one or more of embodiments 29-34, wherein the therapeutic duration is from about 1.0 second to about 5.0 minutes; or further comprising, changing the ultraviolet wavelength, the ultraviolet intensity, or the ultraviolet angle of incidence, or any combination thereof, during an adjustment duration of from about 0.1 second to about 2.0 minutes before, during, or after the therapeutic duration; or wherein the subject is a human being or a mammal.

Embodiment 31. The method of one or more of embodiments 29-34, further comprising:

before, during, or after directing the ultraviolet light into the eye of the subject, reducing inflammation or treating a wound by directing the non-ultraviolet light, including infrared light, into the eye of the subject; or locating an infection area of the eye of the subject and directing the ultraviolet light onto the infection area; or locating and mapping an infection area of the eye of the subject by directing the non-ultraviolet light into the eye of the subject and changing the ultraviolet wavelength, the ultraviolet intensity, or the ultraviolet angle of incidence, or any combination thereof; or wherein the housing contains a processor, wherein the processor is operatively connected to the ultraviolet light source, the non-ultraviolet light source, the camera module, or the eye module, or any combination thereof, and changing the ultraviolet wavelength, the ultraviolet intensity, or the ultraviolet angle of incidence, or any combination thereof, during an adjustment duration of from about 0.10 second to about 2.0 minutes by executing a machine-readable code; or wherein the housing contains a processor, wherein the processor is operatively connected to the ultraviolet light source, the non-ultraviolet light source, the camera module, or the eye module, or any combination thereof, and changing the ultraviolet wavelength, the ultraviolet intensity, or the ultraviolet angle of incidence, or any combination thereof, during an adjustment duration of from about 0.10 second to about 2.0 minutes by transmitting a signal from the processor to an actuator, wherein the actuator is operatively connected to the ultraviolet light source, the non-ultraviolet light source, the camera module, or the eye module, or any combination thereof.

Embodiment 32. The method of one or more of embodiments 29-34, wherein the housing contains a processor, diagnosing the corneal infection by;

directing the non-ultraviolet light into the eye of the subject, detecting a reflected light from the eye of the subject in the camera module, and gathering reflected light data by measuring a reflected wavelength, a reflected intensity, and a reflected light position within an area of the eye of the subject, comparing the reflected light data to a database of corneal infections; and forming a diagnosis by comparing the reflected light data to a type of corneal infection; or forming an infection area data map of the eye by comparing the reflected light data to normal eye data, a database of corneal infections, or both; or any combination thereof.

Embodiment 33. The method of one or more of embodiments 29-34, further comprising:

after forming the diagnosis, changing the ultraviolet wavelength, the ultraviolet intensity, or the ultraviolet angle of incidence, or any combination thereof, based on the reflected light data, the type of corneal infection, or both; or after forming the infection area map, directing from about 50% to 100% of the ultraviolet light onto a mapped infection area of the eye of the subject, wherein the mapped infection area of the eye corresponds to or matches the infection area data map; or any combination thereof.

Embodiment 34. The method of one or more of embodiments 29-34, further comprising:

before, during, or after directing the ultraviolet light into the eye of the subject, directing the non-ultraviolet light into the eye of the subject; or locating an abraded area of the eye of the subject and directing the ultraviolet light, infrared light, or both, onto the abraded area; or locating an abraded area of the eye of the subject by directing the non-ultraviolet light into the eye of the subject and changing the ultraviolet wavelength, the ultraviolet intensity, or the ultraviolet angle of incidence, the infrared wavelength, the infrared intensity, or the infrared angle of incidence, or any combination thereof; or wherein the housing contains a processor, wherein the processor is operatively connected to the ultraviolet light source, the non-ultraviolet light source, the camera module, or the eye module, or any combination thereof, and changing the ultraviolet wavelength, the ultraviolet intensity, or the ultraviolet angle of incidence, or any combination thereof, during an adjustment duration of from about 0.10 second to about 2.0 minutes by executing a machine-readable code; or wherein the housing contains a processor, wherein the processor is operatively connected to the ultraviolet light source, the non-ultraviolet light source, the camera module, or the eye module, or any combination thereof, and changing the ultraviolet wavelength, the ultraviolet intensity, or the ultraviolet angle of incidence, or any combination thereof, during an adjustment duration of from about 0.10 second to about 2.0 minutes by transmitting a signal from the processor to an actuator, wherein the actuator is operatively connected to the ultraviolet light source, the non-ultraviolet light source, the camera module, or the eye module, or any combination thereof.

Embodiment 35: Use of a therapeutic device of one or more of embodiments 1-8 or 15 or 21-28.

Embodiment 36: The method of embodiment 35, providing a therapeutic device, wherein the therapeutic device includes, a housing including an eye module; a camera module mounted in the housing and configured to detect light from the eye module; a non-ultraviolet light source configured to direct non-ultraviolet light through the eye module; and an ultraviolet light source configured to direct ultraviolet light through the eye module at an ultraviolet wavelength, an ultraviolet intensity, and an ultraviolet angle of incidence, wherein the ultraviolet light source is configured to change the ultraviolet wavelength within an ultraviolet range of from about 200 nm to about 300 nm, to change the ultraviolet intensity within an ultraviolet intensity range of from about 2.0 $mJ/cm^2$ to about 1,500 $mJ/cm^2$, or to change the ultraviolet angle of incidence within an ultraviolet angle range of from 0° to 90°, or any combination thereof; and changing the ultraviolet wavelength, the ultraviolet intensity, or the ultraviolet angle of incidence, or any combination thereof, during an adjustment duration of from about 0.1 second to about 2.0 minutes before, during, or after the therapeutic duration

EXAMPLES

Device

Light-emitting diodes at wavelengths 235 nm and 255 nm were identified and ordered from Silanna UV (Brisbane, AU). The datasheets and modeling software (PHOTOPIA®) were used to determine how many LEDs would be needed to provide the necessary power during a 15-second duration. It was determined that when driving the LEDs at a current level of 100 mA, a minimum of 3 LEDs would be needed to provide sufficient irradiation of a spot with a diameter of 1 cm. It was also found that using additional lenses could increase the illuminating power of the LEDs. Two such lenses that could achieve this were identified at EDMUND OPTICS® (Barrington, NJ), both made of fused silica and coated with a UV-anti-reflective coating: an 18-mm diameter lens with 20-mm focal length (used in pairs) and a 15-mm lens with a numerical aperture of 0.6 and effective focal length of 12.5 mm (used as a single lens). Modeling software was used to determine the optimal distance to position these from the LEDs and from the eye. As an alternative to lenses, a reflective coating was also identified to use to focus the beam of the bare LEDs.

The visible light source selected for the device was a NEOPIXEL® RGB (red/green/blue) (Berkeley, CA) addressable LED ring made by ADAFRUIT® (Brooklyn, NY). The infrared light source was infrared LEDs emitting light at 940 nm sold by HILETGO (Shenzhen, China).

The camera for the device was the RASPBERRY PI® (Pencoed, Wales) High Quality Camera Module paired with an Arducam C-mount 12 mega-pixel lens with 16 mm focal length.

The processor chosen to control the LEDs and other components was a RASPBERRY PI®. Software to control the components and create a user interface was written in Python. The machine learning algorithm to automatically identify probable pathogens can be developed using thousands of images of corneal ulcers. The official RASPBERRY PI® 5 power supply was used to provide power to the processor, the visible and IR LEDs, the camera, and touchscreen.

The device touchscreen was a 4.3-inch capacitive touchscreen using a DSI connection ordered from IPISTBIT® (Shenzhen, China). The screen had 800×480 pixel resolution and could be powered by the attached processor.

SOLIDWORKS® (Delaware, USA) computer-aided design software was used to create a custom designed enclosure to contain the parts. This was 3D-printed and assembled using machine screws. The handle was a repurposed tripod handle screwed into the base of the device.

The current embodiment required a DC power supply to supply constant current to the UV LEDs. The device can contain an integrated printed circuit board with a constant current driver to control the LED circuit and an integrated lithium-ion USB-rechargeable power supply. The handle and enclosure can be custom designed in CAD to contain the components and can ultimately be injection molded rather than 3D printed.

The device can be tested on in vitro samples of fungi and bacteria to confirm its efficacy destroying pathogens.

Device Example 1—Dual-Wavelength Far-UVC Array With Optic Lenses

In one embodiment, the therapeutic device used two different far-UVC light-emitting diodes (LEDs) from Silanna UV (Brisbane, AUS). A first set of LEDs were Silanna 235 nm SF1 series parabolic LEDs, and a second set of LEDs were Silanna 230 nm SF2 TO-9 ball-lens LEDs. The datasheets for both LED families and optical modeling software (e.g., PHOTOPIA®) were used to determine the number of LEDs and the drive current needed to provide a desired radiant exposure (for example, at least about 100 mJ/cm$^2$) to a spot approximately 1 cm in diameter during a treatment duration of approximately 15 seconds. When driving the LEDs at a constant current of about 100 mA, it was determined that an array of at least one SF1 235 nm LED and one SF2 230 nm LED provided sufficient irradiance to the 1 cm spot while allowing the controller to select either a predominantly 230 nm spectrum, a predominantly 235 nm spectrum, or a combined spectrum by turning selected LEDs on or off or varying delivered voltage.

As in the base embodiment, fused-silica lenses from EDMUND OPTICS® (Barrington, NJ) were used to increase the irradiance at the corneal surface. The lenses included an 18-mm diameter, 20-mm focal length UV-AR coated double-convex lens (used in pairs) and a 15-mm diameter, numerical aperture 0.6, 12.5-mm effective focal length UV-AR coated lens (used singly). The modeling software was used to determine the optimal spacing between the SF1/SF2 LED packages, the lenses, and the corneal plane so as to obtain an approximately uniform irradiance profile across the 1-cm treatment zone while maintaining a rapid fall-off of irradiance outside of that zone. In some implementations, the LEDs were mounted to evaluation boards or custom printed circuit boards (PCBs), and the optical train was held in a cylindrical lens tube and associated mounts as described above.

Device Example 2—Optimized Far-UVC Optics

In another embodiment, the optical design of the ultraviolet subsystem was performed using ANSYS® ZEMAX® optical modeling software (e.g., ZEMAX® OPTICSTUDIO®) instead of PHOTOPIA®. In this embodiment, two Silanna 235 nm SF1 series parabolic LEDs were positioned on a circular PCB with their emitting surfaces oriented toward a fused-silica collimating lens. The ZEMAX® model included the measured far-UVC emission profile of the SF1 LED package, the refractive indices and dispersion of the fused-silica lenses at 230-255 nm, and the geometry of the eye adapter and light source opening as described above. The software was used to optimize LED-to-lens spacing, lens-to-cornea spacing, and lens diameter to: (i) maximize irradiance over a nominal 1-cm-diameter treatment zone, (ii) limit the fraction of light propagating toward the pupillary axis beyond a preset angular envelope, and (iii) minimize reflective losses at internal surfaces.

The ZEMAX®-optimized design resulted in a single 18-mm diameter, 20-mm focal-length UV-AR coated lens used in combination with a 15-mm NA 0.6, 12.5-mm effective focal-length lens, with both lenses held in a stacked configuration and separated by a modeled distance of approximately 5-15 mm. In some embodiments, the same ZEMAX® model was used to evaluate alternative LED counts (for example, from one to five LEDs) and alternative LED peak wavelengths (for example, about 230 nm, about 235 nm, and about 255 nm), demonstrating that the spectral mix and dose at the corneal surface could be adjusted by selective activation of individual LED channels without changing the mechanical design of the eye module.

Device Example 3—In-Line Camera-Over-LED Configuration Corresponding to FIGS. 8A and 8B In a further embodiment corresponding to FIGS. 8A and 8B, the therapeutic device was configured in a compact, in-line form factor in which the camera module and non-ultraviolet light sources were positioned above a linear or clustered array of far-UVC LEDs within a common forward-facing plane. The housing defined a generally cylindrical eye module terminating in a circular opening sized to receive the subject's orbital region. A camera module was located on the upper portion of the forward face of the housing, with its lens aligned along a central imaging axis directed toward the light source opening. An annular array of visible and/or infrared non-ultraviolet LEDs (for example, an RGB NEOPIXEL® ring and 940-nm infrared LEDs) was mounted around the camera lens to form a ring light for illumination of the eye and for alignment.

Beneath the camera and ring light, three far-UVC LEDs (for example, Silanna SF1 235 nm parabolic LEDs, Silanna SF2 230 nm TO-9 ball-lens LEDs, or a combination thereof) were mounted in a linear array within the housing, with their emission axes directed generally parallel to the imaging axis and toward the light source opening. In this embodiment, no dichroic mirror or other reflective element was used; instead, the far-UVC beams exited directly through the eye module and were confined by the geometry and internal baffling of the eye adapter. The device relied on the close working distance between the LED array and the corneal surface (10-30 mm), together with the LED package optics and any optional fused-silica collimating lens immediately in front of the LEDs, to define the treatment zone.

The ring light surrounding the camera lens corresponded to ring light 828 in FIG. 8B, the camera lens corresponded to reference 826, and the far-UVC LEDs corresponded to first and second LEDs 830, 832 and any additional LEDs positioned beneath the camera. The processor controlled each LED independently, allowing different spectral combinations or dose levels to be delivered by turning individual far-UVC LEDs on or off and by modulating their drive currents.

Device Example 4—Processor Based Control Electronics With Camera Module

In another embodiment, the processor that controlled the LEDs, camera, touchscreen, and other components was a RASPBERRY PI® 4 Model B single-board computer (Pencoed, Wales) as specified in the bill of materials. The RASPBERRY PI® Pi 4B provided general-purpose input/output (GPIO) pins to control one or more constant-current LED driver circuits for the far-UVC LEDs and the non-ultraviolet LED arrays, and communicated with the camera module and touchscreen over standard interfaces (for example, CSI and DSI, respectively).

Software to control the components, implement the treatment timing, and provide a graphical user interface was written in Python and executed on the RASPBERRY PI® 4B.

In one implementation, the camera was the RASPBERRY PI® High Quality (HQ) Camera Module paired with an ARDUCAM® C-mount 12-megapixel lens with 16-mm focal length as described above. In alternative implementations, the HQ Camera Module was replaced with another RASPBERRY PI®-compatible camera module (for example, a RASPBERRY PI® camera module meeting the requirements in the bill of materials: at least 8-megapixel resolution, compatibility with the RASPBERRY PI® 4B CSI interface, and the ability to focus at working distances of less than about 10 cm). Any such camera module could be paired with interchangeable macro lenses or close-focus filters to provide sufficient magnification and clarity for corneal imaging.

The RASPBERRY PI® 4B was powered by a USB-rechargeable lithium-ion battery pack (for example, a RASPBERRY PI®-specific battery pack as listed in the bill of materials) capable of supplying the required voltage and current to simultaneously operate the processor, touchscreen, camera, far-UVC LED driver circuits, and non-ultraviolet LEDs. A custom PCB in the handle of the device integrated the constant-current drivers for the far-UVC LEDs, power-conditioning circuitry, and interfaces to the RASPBERRY PI® 4B. The handle and enclosure were designed in SOLIDWORKS® and 3D-printed for prototyping, with the intention that they may be subsequently manufactured by injection molding.

Device Example 5—Integrated Battery-Powered Constant-Current Driver

In yet another embodiment, the far-UVC LED array (for example, the SF1/SF2 combination described above) was powered by an integrated constant-current driver circuit located on a PCB within the handle of the device. The driver accepted power from an internal lithium-ion battery pack that was rechargeable via a USB-C connector on the base of the handle, eliminating the need for an external DC bench supply. The constant-current driver maintained a stable LED drive current (for example, about 50-350 mA per LED, depending on the desired output) over the full discharge range of the battery and communicated status information (for example, LED current, voltage, and temperature) back to the RASPBERRY PI® processor over an $I^2C$ or SPI interface. The processor used this information, together with camera-acquired images and the treatment algorithm, to adjust LED drive current in real time and to terminate the treatment if preset temperature or dose limits were reached.

Method

The therapeutic device described herein can be used to treat corneal abrasion or infections when used by a clinician. The handheld device is equipped with a UV light source (e.g. multiple UV-C LEDs), an infrared source (e.g. infrared LEDs), and a visible light source (e.g. visible light LEDs). The clinician powers on the device, which turns on the camera that displays a live image on the attached LCD touchscreen. The clinician positions the device in front of the patient's eye so the eye is covered by the eye adaptor. The clinician confirms device positioning by looking through the touchscreen. The clinician initiates the diagnostic and treatment algorithm using the touchscreen. The visible and infrared light sources illuminate the eye and enable the algorithm to precisely identify the bounds of the abrasion or infectious area as well as pathogen types that are present. Once identification is complete, the clinician can initiate a treatment cycle on the device, which automatically selects one or more wavelengths of UV (e.g. 235 nm and 255 nm) and infrared light (e.g. 850 nm) to emit on to the affected region of the eye. The device algorithm determines the appropriate duration of time for treatment (e.g. 15 seconds) and then turns off the light sources. The UV acts to destroy pathogens in the eye, while the IR works to reduce inflammation and promote healing. This cycle may be repeated later during the same day or in subsequent days to ameliorate infection.

What is claimed is:

1. A therapeutic device for treating a corneal abrasion, a corneal infection, or prophylaxis of a corneal infection, or any combination thereof, comprising:
- a housing including an eye module;
- a camera module mounted in the housing and configured to detect light from the eye module;
- a non-ultraviolet light source configured to direct non-ultraviolet light through the eye module; and
- an ultraviolet light source configured to direct ultraviolet light through the eye module at an ultraviolet wavelength, an ultraviolet intensity, and an ultraviolet angle of incidence,
- wherein the ultraviolet light source is configured to change the ultraviolet wavelength within an ultraviolet range of from about 200 nm to about 300 nm, to change the ultraviolet intensity within an ultraviolet intensity range of from about 2.0 mJ/cm$^2$ to about 1,500 mJ/cm$^2$, or to change the ultraviolet angle of incidence within an ultraviolet angle range of from 0° to 90°, or any combination thereof, and
- wherein the housing includes a UV mirror, wherein the UV mirror includes a dichroic mirror, wherein the UV mirror is located between the eye module and the camera module, wherein the UV mirror is configured to direct the ultraviolet light from the ultraviolet light source through the eye module,
- wherein the ultraviolet light source includes an ultraviolet light emitting diode, an array of ultraviolet light emitting diodes, an excimer lamp, a laser, or a combination thereof,
- wherein the non-ultraviolet light includes visible light, and
- wherein the non-ultraviolet light source includes a visible light emitting diode, an array of visible light emitting diodes, or any combination thereof.

2. The therapeutic device of claim 1, wherein the eye module is located on an exterior of the housing and includes a light source opening surrounded by an eye adapter, wherein the eye adapter has a ring shape with a raised lip surrounding an eye adapter recess, wherein the eye adapter recess surrounds the light source opening; and wherein the raised lip has a lip diameter or a lip longest distance across the eye adapter of from about 40.0 mm to about 60.0 mm; or wherein the eye adapter recess has an eye adapter depth of about 1.0 cm to about 5.0 cm from the raised lip to the light source opening; or wherein the therapeutic device has a device weight of about 227.0 g to about 1,360.0 g, or wherein the UV mirror is located between the eye module and the ultraviolet light source;

wherein the housing contains an actuator, a frequency doubler, a mechanically rotatable filter, or both, located between the eye module and the non-ultraviolet light source, and configured to convert the non-ultraviolet light into the ultraviolet light; or any combination thereof.

3. The therapeutic device of claim 1, wherein the eye module includes an array of optical fibers, wherein the array of optical fibers is operatively connected to the ultraviolet light source, wherein the ultraviolet light source includes an array of ultraviolet light emitting diodes, an excimer lamp, a laser, or a combination thereof;

wherein emitting portions of the array of optical fibers are mounted around an eye adapter interior surface of the eye module;

wherein an eye module actuator is operatively connected to the eye adapter, the emitting portions, or any combination thereof; and wherein the eye module actuator is configured to change the ultraviolet angle of incidence from the emitting portions by moving the emitting portions along the eye module interior surface; or wherein the eye module actuator is configured to change the ultraviolet angle of incidence from the emitting portions by moving the eye adapter; or wherein the eye module contains one or more movable reflectors capable of changing the angle of incidence relative to the emitting portions;

or any combination thereof.

4. The therapeutic device of claim 1, wherein the ultraviolet light source includes an array of ultraviolet light emitting diodes mounted around an eye adapter interior surface of the eye module, wherein an ultraviolet light emitting diode of the array of ultraviolet light emitting diodes is mounted on an actuator track, and wherein the ultraviolet light emitting diode is configured to change the ultraviolet angle of incidence by moving the ultraviolet light emitting diode along the actuator track; or wherein two or more ultraviolet light emitting diodes of the array of ultraviolet light emitting diodes are mounted on an actuator track, and the two or more ultraviolet light emitting diodes are configured to change the ultraviolet wavelength, the ultraviolet intensity, or the ultraviolet angle of incidence, or any combination thereof, by turning on or off.

5. The therapeutic device of claim 1, wherein the ultraviolet light source includes an array of ultraviolet light emitting diodes mounted around an eye adapter interior surface of the eye module, wherein two or more ultraviolet light emitting diodes of the array of ultraviolet light emitting diodes are configured to change the ultraviolet wavelength, the ultraviolet intensity, or the ultraviolet angle of incidence, or any combination thereof, by turning on or off.

6. The therapeutic device of claim 1, wherein the housing contains a camera module opening surrounding a lens of the camera module, and wherein the non-ultraviolet light source includes an array of infrared light emitting diodes, or a combined array of visible light emitting diodes and infrared light emitting diodes, or any combination thereof, or wherein the non-ultraviolet light source includes a visible light emitting diode capable of emitting light at a visible wavelength of from about 400 nm to about 700 nm; or wherein the non-ultraviolet light source includes an infrared light emitting diode capable of emitting an infrared light at a wavelength of from about 780 nm to about 1,000 nm; or wherein the non-ultraviolet light source is located adjacent to a lens of the camera module; or wherein the non-ultraviolet light source includes an array of visible light emitting diodes adjacent to or round a lens of the camera module;

wherein the non-ultraviolet light source includes an array of infrared light emitting diodes adjacent to or round a lens of the camera module; or any combination thereof.

7. The therapeutic device of claim 1, wherein the housing contains a processor, wherein the processor is operatively connected to a control panel located on the device exterior, or wherein the processor is operatively connected to at least one communication link, or any combination thereof, wherein the communication link includes a short-range wireless connection, a universal serial bus (USB) connection, or a data port; or wherein the camera module includes a charged coupled device or a complementary metal oxide semiconductor (CMOS) image sensor; or a camera lens configured to focus light at a distance of from about 1.0 cm to about 25.0 cm from a surface of the camera lens; or the camera module includes a light transparent protective cover between a surface of the camera lens and the eye module; or wherein the housing contains the ultraviolet light source and the non-ultraviolet light source and one or both of the ultraviolet light source and the non-ultraviolet light source are configured to move along a track or to change ultraviolet intensity or both; or any combination thereof.

8. A method of detecting or treating a corneal abrasion, a corneal infection, or prophylaxis of a corneal infection, or any combination thereof, in a subject in need thereof, comprising:

providing a therapeutic device, wherein the therapeutic device includes, a housing including an eye module; a camera module mounted in the housing and configured to detect light from the eye module; a non-ultraviolet light source configured to direct non-ultraviolet light through the eye module; and an ultraviolet light source configured to direct ultraviolet light through the eye module at an ultraviolet wavelength, an ultraviolet intensity, and an ultraviolet angle of incidence, wherein the ultraviolet light source is configured to change the ultraviolet wavelength within an ultraviolet range of from about 200 nm to about 300 nm, to change the ultraviolet intensity within an ultraviolet intensity range of from about 2.0 $mJ/cm^2$ to about 1,500 $mJ/cm^2$, or to change the ultraviolet angle of incidence within an ultraviolet angle range of from 0° to 90°, or any combination thereof, and wherein the housing includes a UV mirror, wherein the UV mirror includes a dichroic mirror, wherein the UV mirror is located between the eye module and the camera module, wherein the UV mirror is configured to direct the ultraviolet light from the ultraviolet light source through the eye module, wherein the ultraviolet light source includes an ultraviolet light emitting diode, an array of ultraviolet light emitting diodes, an excimer lamp, a laser, or a combination thereof, wherein the non-ultraviolet light includes visible light, and wherein the non-ultraviolet light source includes a visible light emitting diode, an array of visible light emitting diodes, or any combination thereof; and directing the ultraviolet light into the eye of the subject at the ultraviolet wavelength, the ultraviolet intensity, or the ultraviolet angle of incidence, or any combination thereof, for a therapeutic duration.

9. The method of claim 8, wherein the therapeutic duration is from about 1.0 second to about 5.0 minutes; or further comprising, changing the ultraviolet wavelength, the ultraviolet intensity, or the ultraviolet angle of incidence, or any combination thereof, during an adjustment duration of from about 0.1 second to about 2.0 minutes before, during, or after the therapeutic duration; or wherein the subject is a human being or a mammal.

10. The method of claim 8, further comprising:

before, during, or after directing the ultraviolet light into the eye of the subject, reducing inflammation or microbial burden; or treating a wound by directing the non-ultraviolet light, including infrared light, into the eye of the subject; or before or during directing the ultraviolet light into the eye of the subject, contacting the eye of the subject with hypochlorous acid;

locating an infection area of the eye of the subject and directing the ultraviolet light onto the infection area; or locating and mapping an infection area of the eye of the subject by directing the non-ultraviolet light into the eye of the subject and changing the ultraviolet wavelength, the ultraviolet intensity, or the ultraviolet angle of incidence, or any combination thereof; or wherein the housing contains a processor, wherein the processor is operatively connected to the ultraviolet light source, the non-ultraviolet light source, the camera module, or the eye module, or any combination thereof, and changing the ultraviolet wavelength, the ultraviolet intensity, or the ultraviolet angle of incidence, or any combination thereof, during an adjustment duration of from about 0.10 second to about 2.0 minutes by executing a machine-readable code; or wherein the housing contains a processor, wherein the processor is operatively connected to the ultraviolet light source, the non-ultraviolet light source, the camera module, or the eye module, or any combination thereof, and changing the ultraviolet wavelength, the ultraviolet intensity, or the ultraviolet angle of incidence, or any combination thereof, during an adjustment duration of from about 0.10 second to about 2.0 minutes by transmitting a signal from the processor to an actuator, wherein the actuator is operatively connected to the ultraviolet light source, the non-ultraviolet light source, the camera module, or the eye module, or any combination thereof.

11. The method of claim 8, wherein the housing contains a processor, diagnosing the corneal infection by:

directing the non-ultraviolet light into the eye of the subject, detecting a reflected light from the eye of the subject in the camera module, and gathering reflected light data by measuring a reflected wavelength, a reflected intensity, and a reflected light position within an area of the eye of the subject, comparing the reflected light data to a database of corneal infections; and forming a diagnosis by comparing the reflected light data to a type of corneal infection.

12. The method of claim 11, further comprising:

after forming the diagnosis, changing the ultraviolet wavelength, the ultraviolet intensity, or the ultraviolet angle of incidence, or any combination thereof, based on the reflected light data, the type of corneal infection, or both; or forming an infection area data map of the eye by comparing the reflected light data to normal eye data, a database of corneal infections, or both, after forming the infection area map, directing from about 50% to 100% of the ultraviolet light onto a mapped infection area of the eye of the subject, wherein the mapped infection area of the eye corresponds to or matches the infection area data map; or any combination thereof.

13. The method of claim 8, further comprising:

before, during, or after directing the ultraviolet light into the eye of the subject, directing the non-ultraviolet light into the eye of the subject; or locating an abraded area of the eye of the subject and directing the ultraviolet light, infrared light, or both, onto the abraded area; or locating an abraded area of the eye of the subject by directing the non-ultraviolet light into the eye of the subject and changing the ultraviolet wavelength, the ultraviolet intensity, or the ultraviolet angle of incidence, the infrared wavelength, the infrared intensity, or the infrared angle of incidence, or any combination thereof; or wherein the housing contains a processor, wherein the processor is operatively connected to the ultraviolet light source, the non-ultraviolet light source, the camera module, or the eye module, or any combination thereof, and changing the ultraviolet wavelength, the ultraviolet intensity, or the ultraviolet angle of incidence, or any combination thereof, during an adjustment duration of from about 0.10 second to about 2.0 minutes by executing a machine-readable code; or wherein the housing contains a processor, wherein the processor is operatively connected to the ultraviolet light source, the non-ultraviolet light source, the camera module, or the eye module, or any combination thereof, and changing the ultraviolet wavelength, the ultraviolet intensity, or the ultraviolet angle of incidence, or any combination thereof, during an adjustment duration of from about 0.10 second to about 2.0 minutes by transmitting a signal from the processor to an actuator, wherein the actuator is operatively connected to the ultraviolet light source, the non-ultraviolet light source, the camera module, or the eye module, or any combination thereof.

14. The therapeutic device of claim 1, wherein the ultraviolet light source includes an array of ultraviolet light emitting diodes mounted around an eye adapter interior surface of the eye module, or mounted within the housing and directed toward the light source opening, or both; and wherein two or more ultraviolet light emitting diodes of the array of ultraviolet light emitting diodes are configured to change the ultraviolet wavelength, the ultraviolet intensity, or the ultraviolet angle of incidence, or any combination thereof, by turning on or off; or wherein the ultraviolet light source includes an array of ultraviolet light emitting diodes and a non-ultraviolet light source mounted around an eye adapter interior surface of the eye module, or mounted within the housing and directed toward the light source opening, or both; and wherein two or more ultraviolet light emitting diodes of the array of ultraviolet light emitting diodes are configured to change the ultraviolet wavelength, the ultraviolet intensity, or the ultraviolet angle of incidence, or any combination thereof, by turning on or off.

15. The therapeutic device of claim 1, wherein the housing contains an actuator adjustable focal lens, a frequency doubler, a triple filter, one or more rotatable filters, a mechanically rotatable filter, or an aperture, or a combination thereof, located between the eye module and the ultraviolet light source.

16. The therapeutic device of claim 15, wherein the housing contains one or more of the actuator adjustable focal lens, the frequency doubler, the triple filter, one or more rotatable filters, the mechanically rotatable filter, the aperture, or the combination thereof, which are configured to change the ultraviolet wavelength, the ultraviolet intensity, or the ultraviolet angle of incidence, or any combination thereof.

17. The therapeutic device of claim 1, wherein the non-ultraviolet light source includes an array of visible light emitting diodes.

18. The therapeutic device of claim 1, wherein the housing contains a processor, wherein the processor is operatively connected to the ultraviolet light source, the non-ultraviolet light source, the camera module, or the eye module, or any combination thereof, and wherein the processor is configured to change the ultraviolet wavelength, the ultraviolet intensity, or the ultraviolet angle of incidence, or any combination thereof, during an adjustment duration of from about 0.1 second to about 2.0 minutes by executing a computer readable code.

19. The method of claim 8, further comprising:

forming an infection area data map of the eye by comparing the reflected light data to normal eye data, a database of corneal infections, or both.

* * * * *